United States Patent
Shen et al.

(10) Patent No.: US 9,695,463 B2
(45) Date of Patent: Jul. 4, 2017

(54) DNA 5-METHYL CYTOSINE DEMETHYLATION ACTIVITY OF VERTEBRATE DNA METHYLTRANSFERASES

(71) Applicant: Academia Sinica, Taipei (TW)

(72) Inventors: Che-Kun James Shen, Taipei (TW); Chun-Chang Chen, Changhua County (TW)

(73) Assignee: ACADEMIA SINICA, Taipei (TW)

( * ) Notice: Subject to any disclaimer, the term of this patent is extended or adjusted under 35 U.S.C. 154(b) by 171 days.

(21) Appl. No.: 14/647,816

(22) PCT Filed: Dec. 10, 2013

(86) PCT No.: PCT/US2013/074141
§ 371 (c)(1),
(2) Date: May 27, 2015

(87) PCT Pub. No.: WO2014/093351
PCT Pub. Date: Jun. 19, 2014

(65) Prior Publication Data
US 2015/0315628 A1 Nov. 5, 2015

Related U.S. Application Data

(60) Provisional application No. 61/736,180, filed on Dec. 12, 2012.

(51) Int. Cl.
*C12Q 1/48* (2006.01)
*C12Q 1/68* (2006.01)

(52) U.S. Cl.
CPC .......... *C12Q 1/48* (2013.01); *C12Q 1/68* (2013.01); *C12Q 1/6897* (2013.01); *G01N 2333/91011* (2013.01); *G01N 2500/04* (2013.01)

(58) Field of Classification Search
None
See application file for complete search history.

(56) References Cited

U.S. PATENT DOCUMENTS

2005/0003378 A1* 1/2005 Szyf .................. C12Q 1/34
435/6.12
2006/0166909 A1 7/2006 Szyf et al.

OTHER PUBLICATIONS

Chen, CC et al. The Mammalian de Novo DNA Methyltransferases DNMT3A and DNMT3B Are Also DNA 5-Hydroxymethylctosine Dehydroxythethylases. J Biol Chem. Aug. 16, 2012, vol. 287, No. 40, pp. 33116-331121; abstract; p. 33116, right column, second paragraph; p. 33118, figure 1. DOI: 10.10741jbc.C112.406975.

Jost JP et al. 5-Methyldeoxycytidine monophosphate Dearninase and 5-methylcytidyl-DNA Deaminase Activities Are Present in Human Mature Sperm Cells. FEBS Lett. May 22, 2002, vol. 519, pp. 126-134; abstract; p. 128, right column, second to third paragraph. DOI; 10.1 016/S0014-5793(02)02737-0.

Technical Bulletin: pCI and pSI Mammalian Expression Vectors, Instructions for Use of Products E1721 and E1731. Datasheet [online]. Promgea Corportation. Jul. 2009 [retrieved on 14/9-11, 15/9 15/10, Nov. 2, 2014). Retrieved from Internet: <URL: 16/9-11 • 17/9-111, 20/9. https://www.promega.com/resources/protocols/technical-bulletins/0/pci-and-psi-mammalian-expr 20/10 ession-vectors-protocoll>.

* cited by examiner

*Primary Examiner* — David Thomas
(74) *Attorney, Agent, or Firm* — Hsiu-Ming Saunders; Intellectual Property Connections, Inc.

(57) ABSTRACT

Methods for identifying a test agent as a modulator of the active DNA demethylation activity of a DNA methyltransferase are disclosed. The method comprises: a) providing a methylated DNA; b) providing the DNA methyltransferase; c) allowing the methylated DNA to react with the DNA methyltransferase for a sufficient time to perform a demethylation reaction and generate a demethylated DNA product in the presence or absence of a test agent; d) analyzing the extent of demethylation; and d) comparing the extents of the demethylation in the presence and absence of the test agent, and thereby identify the test agent as a modulator of the DNA demethylation activity of the DNA methyltransferase.

20 Claims, 4 Drawing Sheets

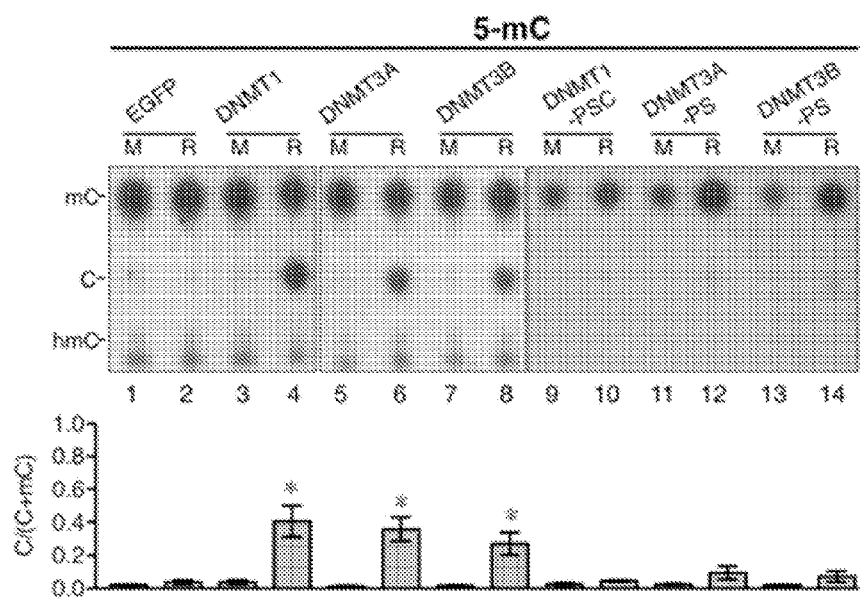
FIG. 1
FIG. 2A
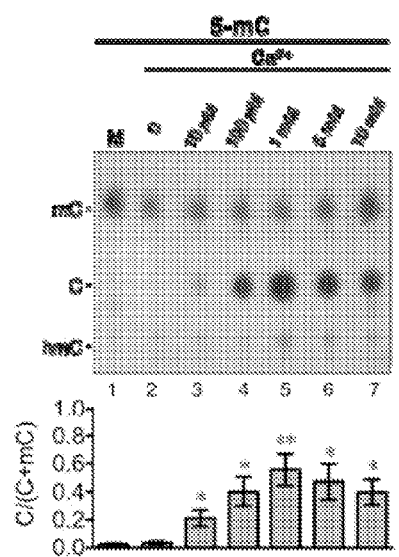
FIG. 2B
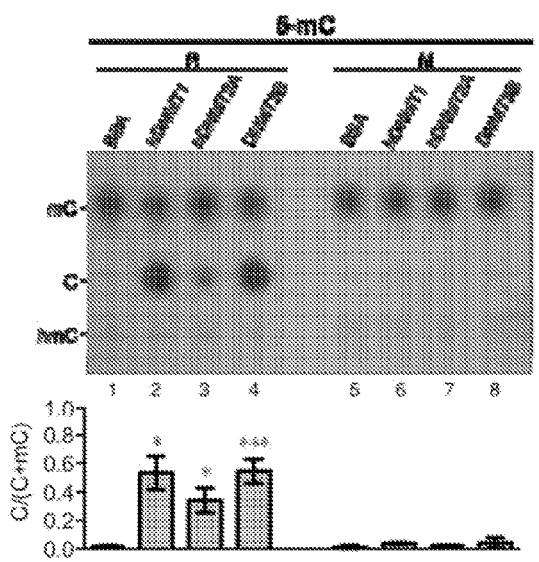

SEQUENCE LISTING

<160> NUMBER OF SEQ ID NOS: 9

<210> SEQ ID NO 1
<211> LENGTH: 2819
<212> TYPE: DNA

<213> ORGANISM: Artificial Sequence
<220> FEATURE:
<223> OTHER INFORMATION: pMR1-8

<400> SEQUENCE: 1

| | | | | | |
|---|---|---|---|---|---|
| cacctaaatt | gtaagcgtta | atattttgtt | aaaattcgcg | ttaaattttt | gttaaatcag | 60 |
| ctcattttt | aaccaatagg | ccgaaatcgg | caaaatccct | tataaatcaa | aagaatagac | 120 |
| cgagataggg | ttgagtgttg | ttccagtttg | gaacaagagt | ccactattaa | agaacgtgga | 180 |
| ctccaacgtc | aaagggcgaa | aaaccgtcta | tcagggcgat | ggcccactac | gtgaaccatc | 240 |
| accctaatca | agttttttgg | ggtcgaggtg | ccgtaaagca | ctaaatcgga | accctaaagg | 300 |
| gagcccccga | tttagagctt | gacggggaaa | gccggcgaac | gtggcgagaa | aggaagggaa | 360 |
| gaaagcgaaa | ggagcgggcg | ctagggcgct | ggcaagtgta | gcggtcacgc | tgcgcgtaac | 420 |
| caccacaccc | gccgcgctta | atgcgccgct | acagggcgcg | tcccattcgc | cattcaggct | 480 |
| gcgcaactgt | tgggaagggc | gatcggtgcg | ggcctcttcg | ctattacgcc | agctggcgaa | 540 |
| agggggatgt | gctgcaaggc | gattaagttg | ggtaacgcca | gggttttccc | agtcacgacg | 600 |
| ttgtaaaacg | acggccagtg | aattgtaata | cgactcacta | tagggcgaat | tggagctcca | 660 |
| ccgcggtggc | ggccgctcta | gaactagtgg | atcccccggg | ctgcaggaat | tgctagcaag | 720 |
| ctttcgagtc | tagaaattcg | atatcaagct | agcctggggt | gcctaatgag | tgagctaact | 780 |
| cacattaatt | gcgttgcgct | cactgcccgc | tttccagtcg | ggaaacctgt | cgtgccagct | 840 |
| gcattaatga | atcggccaac | gcgcgggag | aggcggtttg | cgtattgggc | gctcttccgc | 900 |
| ttcctcgctc | actgactcgc | tgcgctcggt | cgttcggctg | cggcgagcgg | tatcagctca | 960 |
| ctcaaaggcg | gtaatacggt | tatccacaga | atcaggggat | aacgcaggaa | agaacatgtg | 1020 |
| agcaaaaggc | cagcaaaagg | ccaggaaccg | taaaaaggcc | gcgttgctgg | cgttttcca | 1080 |
| taggctccgc | cccctgacg | agcatcacaa | aaatcgacgc | tcaagtcaga | ggtggcgaaa | 1140 |
| cccgacagga | ctataaagat | accaggcgtt | tccccctgga | agctccctcg | tgcgctctcc | 1200 |
| tgttccgacc | ctgccgctta | ccggatacct | gtccgccttt | ctcccttcgg | gaagcgtggc | 1260 |
| gctttctcat | agctcacgct | gtaggtatct | cagttcggtg | taggtcgttc | gctccaagct | 1320 |
| gggctgtgtg | cacgaacccc | ccgttcagcc | cgaccgctgc | gccttatccg | gtaactatcg | 1380 |
| tcttgagtcc | aacccggtaa | gacacgactt | atcgccactg | gcagcagcca | ctggtaacag | 1440 |
| gattagcaga | gcgaggtatg | taggcggtgc | tacagagttc | ttgaagtggt | ggcctaacta | 1500 |
| cggctacact | agaaggacag | tatttggtat | ctgcgctctg | ctgaagccag | ttaccttcgg | 1560 |
| aaaaagagtt | ggtagctctt | gatccggcaa | acaaaccacc | gctggtagcg | gtggtttttt | 1620 |
| tgtttgcaag | cagcagatta | cgcgcagaaa | aaaaggatct | caagaagatc | ctttgatctt | 1680 |
| ttctacgggg | tctgacgctc | agtggaacga | aaactcacgt | taagggattt | tggtcatgag | 1740 |
| attatcaaaa | aggatcttca | cctagatcct | tttaaattaa | aaatgaagtt | ttaaatcaat | 1800 |
| ctaaagtata | tatgagtaaa | cttggtctga | cagttaccaa | tgcttaatca | gtgaggcacc | 1860 |
| tatctcagcg | atctgtctat | ttcgttcatc | catagttgcc | tgactccccg | tcgtgtagat | 1920 |
| aactacgata | cgggagggct | taccatctgg | ccccagtgct | gcaatgatac | cgcgagaccc | 1980 |
| acgctcaccg | gctccagatt | tatcagcaat | aaaccagcca | gccggaaggg | ccgagcgcag | 2040 |
| aagtggtcct | gcaactttat | ccgcctccat | ccagtctatt | aattgttgcc | gggaagctag | 2100 |
| agtaagtagt | tcgccagtta | atagtttgcg | caacgttgtt | gccattgcta | caggcatcgt | 2160 |
| ggtgtcacgc | tcgtcgtttg | gtatggcttc | attcagctcc | ggttcccaac | gatcaaggcg | 2220 |

-continued

```
agttacatga tcccccatgt tgtgcaaaaa agcggttagc tccttcggtc ctccgatcgt    2280
tgtcagaagt aagttggccg cagtgttatc actcatggtt atggcagcac tgcataattc    2340
tcttactgtc atgccatccg taagatgctt ttctgtgact ggtgagtact caaccaagtc    2400
attctgagaa tagtgtatgc ggcgaccgag ttgctcttgc ccggcgtcaa tacgggataa    2460
taccgcgcca catagcagaa cttttaaagt gctcatcatt ggaaaacgtt cttcggggcg    2520
aaaactctca aggatcttac cgctgttgag atccagttcg atgtaaccca ctcgtgcacc    2580
caactgatct tcagcatctt ttactttcac cagcgtttct gggtgagcaa aacaggaag    2640 gcaaaatgcc gcaaaaaagg gaataagggc gacacgaaaa tgttgaatac tcatactctt    2700
cctttttcaa tattattgaa gcatttatca gggttattgt ctcatgagcg gatacatatt    2760
tgaatgtatt tagaaaaata aacaataggg gttccgcgca catttccccc gaaaagtgc     2819
```

<210> SEQ ID NO 2
<211> LENGTH: 21
<212> TYPE: DNA
<213> ORGANISM: Artificial Sequence
<220> FEATURE:
<223> OTHER INFORMATION: pMR1-8 F

<400> SEQUENCE: 2

```
aaagatacca ggcgtttccc c                                                21
```

<210> SEQ ID NO 3
<211> LENGTH: 23
<212> TYPE: DNA
<213> ORGANISM: Artificial Sequence
<220> FEATURE:
<223> OTHER INFORMATION: pMR1-8 R

<400> SEQUENCE: 3

```
gagttttcgt tccactgagc gtc                                              23
```

<210> SEQ ID NO 4
<211> LENGTH: 1632
<212> TYPE: PRT
<213> ORGANISM: Homo sapiens

<400> SEQUENCE: 4

```
Met Pro Ala Arg Thr Ala Pro Ala Arg Val Pro Thr Leu Ala Val Pro
1               5                   10                  15

Ala Ile Ser Leu Pro Asp Asp Val Arg Arg Arg Leu Lys Asp Leu Glu
            20                  25                  30

Arg Asp Ser Leu Thr Glu Lys Glu Cys Val Lys Glu Lys Leu Asn Leu
        35                  40                  45

Leu His Glu Phe Leu Gln Thr Glu Ile Lys Asn Gln Leu Cys Asp Leu
    50                  55                  60

Glu Thr Lys Leu Arg Lys Glu Glu Leu Ser Glu Gly Tyr Leu Ala
65                  70                  75                  80

Lys Val Lys Ser Leu Leu Asn Lys Asp Leu Ser Leu Glu Asn Gly Ala
                85                  90                  95

His Ala Tyr Asn Arg Glu Val Asn Gly Arg Leu Glu Asn Gly Asn Gln
            100                 105                 110

Ala Arg Ser Glu Ala Arg Arg Val Gly Met Ala Asp Ala Asn Ser Pro
        115                 120                 125

Pro Lys Pro Leu Ser Lys Pro Arg Thr Pro Arg Arg Ser Lys Ser Asp
    130                 135                 140
```

```
Gly Glu Ala Lys Arg Ser Arg Asp Pro Pro Ala Ser Ala Ser Gln Val
145                 150                 155                 160

Thr Gly Ile Arg Ala Glu Pro Ser Pro Ser Pro Arg Ile Thr Arg Lys
                165                 170                 175

Ser Thr Arg Gln Thr Thr Ile Thr Ser His Phe Ala Lys Gly Pro Ala
            180                 185                 190

Lys Arg Lys Pro Gln Glu Glu Ser Glu Arg Ala Lys Ser Asp Glu Ser
                195                 200                 205

Ile Lys Glu Glu Asp Lys Asp Gln Asp Glu Lys Arg Arg Arg Val Thr
            210                 215                 220

Ser Arg Glu Arg Val Ala Arg Pro Leu Pro Ala Glu Glu Pro Glu Arg
225                 230                 235                 240

Ala Lys Ser Gly Thr Arg Thr Glu Lys Glu Glu Arg Asp Glu Lys
                245                 250                 255

Glu Glu Lys Arg Leu Arg Ser Gln Thr Lys Glu Pro Thr Pro Lys Gln
                260                 265                 270

Lys Leu Lys Glu Glu Pro Asp Arg Glu Ala Arg Ala Gly Val Gln Ala
            275                 280                 285

Asp Glu Asp Glu Asp Gly Asp Glu Lys Asp Glu Lys Lys His Arg Ser
            290                 295                 300

Gln Pro Lys Asp Leu Ala Ala Lys Arg Arg Pro Glu Glu Lys Glu Pro
305                 310                 315                 320

Glu Lys Val Asn Pro Gln Ile Ser Asp Glu Lys Asp Glu Asp Glu Lys
                325                 330                 335

Glu Glu Lys Arg Arg Lys Thr Thr Pro Lys Glu Pro Thr Glu Lys Lys
                340                 345                 350

Met Ala Arg Ala Lys Thr Val Met Asn Ser Lys Thr His Pro Pro Lys
            355                 360                 365

Cys Ile Gln Cys Gly Gln Tyr Leu Asp Asp Pro Asp Leu Lys Tyr Gly
            370                 375                 380

Gln His Pro Pro Asp Ala Val Asp Glu Pro Gln Met Leu Thr Asn Glu
385                 390                 395                 400

Lys Leu Ser Ile Phe Asp Ala Asn Glu Ser Gly Phe Glu Ser Tyr Glu
                405                 410                 415

Ala Leu Pro Gln His Lys Leu Thr Cys Phe Ser Val Tyr Cys Lys His
                420                 425                 430

Gly His Leu Cys Pro Ile Asp Thr Gly Leu Ile Glu Lys Asn Ile Glu
            435                 440                 445

Leu Phe Phe Ser Gly Ser Ala Lys Pro Ile Tyr Asp Asp Pro Ser
450                 455                 460

Leu Glu Gly Gly Val Asn Gly Lys Asn Leu Gly Pro Ile Asn Glu Trp
465                 470                 475                 480

Trp Ile Thr Gly Phe Asp Gly Gly Glu Lys Ala Leu Ile Gly Phe Ser
            485                 490                 495

Thr Ser Phe Ala Glu Tyr Ile Leu Met Asp Pro Ser Pro Glu Tyr Ala
            500                 505                 510

Pro Ile Phe Gly Leu Met Gln Glu Lys Ile Tyr Ile Ser Lys Ile Val
            515                 520                 525

Val Glu Phe Leu Gln Ser Asn Ser Asp Ser Thr Tyr Glu Asp Leu Ile
            530                 535                 540

Asn Lys Ile Glu Thr Thr Val Pro Pro Ser Gly Leu Asn Leu Asn Arg
545                 550                 555                 560
```

-continued

```
Phe Thr Glu Asp Ser Leu Leu Arg His Ala Gln Phe Val Val Glu Gln
            565                 570                 575
Val Glu Ser Tyr Asp Glu Ala Gly Asp Ser Asp Glu Gln Pro Ile Phe
        580                 585                 590
Leu Thr Pro Cys Met Arg Asp Leu Ile Lys Leu Ala Gly Val Thr Leu
    595                 600                 605
Gly Gln Arg Arg Ala Gln Ala Arg Arg Gln Thr Ile Arg His Ser Thr
610                 615                 620
Arg Glu Lys Asp Arg Gly Pro Thr Lys Ala Thr Thr Thr Lys Leu Val
625                 630                 635                 640
Tyr Gln Ile Phe Asp Thr Phe Phe Ala Glu Gln Ile Glu Lys Asp Asp
            645                 650                 655
Arg Glu Asp Lys Glu Asn Ala Phe Lys Arg Arg Cys Gly Val Cys
        660                 665                 670
Glu Val Cys Gln Gln Pro Glu Cys Gly Lys Cys Lys Ala Cys Lys Asp
    675                 680                 685
Met Val Lys Phe Gly Gly Ser Gly Arg Ser Lys Gln Ala Cys Gln Glu
    690                 695                 700
Arg Arg Cys Pro Asn Met Ala Met Lys Glu Ala Asp Asp Asp Glu Glu
705                 710                 715                 720
Val Asp Asp Asn Ile Pro Glu Met Pro Ser Pro Lys Lys Met His Gln
            725                 730                 735
Gly Lys Lys Lys Lys Gln Asn Lys Asn Arg Ile Ser Trp Val Gly Glu
            740                 745                 750
Ala Val Lys Thr Asp Gly Lys Lys Ser Tyr Tyr Lys Lys Val Cys Ile
        755                 760                 765
Asp Ala Glu Thr Leu Glu Val Gly Asp Cys Val Ser Val Ile Pro Asp
    770                 775                 780
Asp Ser Ser Lys Pro Leu Tyr Leu Ala Arg Val Thr Ala Leu Trp Glu
785                 790                 795                 800
Asp Ser Ser Asn Gly Gln Met Phe His Ala His Trp Phe Cys Ala Gly
            805                 810                 815
Thr Asp Thr Val Leu Gly Ala Thr Ser Asp Pro Leu Glu Leu Phe Leu
        820                 825                 830
Val Asp Glu Cys Glu Asp Met Gln Leu Ser Tyr Ile His Ser Lys Val
    835                 840                 845
Lys Val Ile Tyr Lys Ala Pro Ser Glu Asn Trp Ala Met Glu Gly Gly
    850                 855                 860
Met Asp Pro Glu Ser Leu Leu Glu Gly Asp Asp Gly Lys Thr Tyr Phe
865                 870                 875                 880
Tyr Gln Leu Trp Tyr Asp Gln Asp Tyr Ala Arg Phe Glu Ser Pro Pro
            885                 890                 895
Lys Thr Gln Pro Thr Glu Asp Asn Lys Phe Lys Phe Cys Val Ser Cys
        900                 905                 910
Ala Arg Leu Ala Glu Met Arg Gln Lys Glu Ile Pro Arg Val Leu Glu
    915                 920                 925
Gln Leu Glu Asp Leu Asp Ser Arg Val Leu Tyr Tyr Ser Ala Thr Lys
930                 935                 940
Asn Gly Ile Leu Tyr Arg Val Gly Asp Gly Val Tyr Leu Pro Pro Glu
945                 950                 955                 960
Ala Phe Thr Phe Asn Ile Lys Leu Ser Ser Pro Val Lys Arg Pro Arg
            965                 970                 975
Lys Glu Pro Val Asp Glu Asp Leu Tyr Pro Glu His Tyr Arg Lys Tyr
```

-continued

```
                980             985                990
Ser Asp Tyr Ile Lys Gly Ser Asn  Leu Asp Ala Pro Glu  Pro Tyr Arg
            995             1000              1005

Ile Gly  Arg Ile Lys Glu Ile  Phe Cys Pro Lys  Ser Asn Gly
    1010              1015              1020

Arg Pro  Asn Glu Thr Asp Ile  Lys Ile Arg Val Asn  Lys Phe Tyr
    1025              1030              1035

Arg Pro  Glu Asn Thr His Lys  Ser Thr Pro Ala Ser  Tyr His Ala
    1040              1045              1050

Asp Ile  Asn Leu Leu Tyr Trp  Ser Asp Glu Ala  Val Val Asp
    1055              1060              1065

Phe Lys  Ala Val Gln Gly Arg  Cys Thr Val Glu Tyr  Gly Glu Asp
    1070              1075              1080

Leu Pro  Glu Cys Val Gln Val  Tyr Ser Met Gly Gly  Pro Asn Arg
    1085              1090              1095

Phe Tyr  Phe Leu Glu Ala Tyr  Asn Ala Lys Ser Lys  Ser Phe Glu
    1100              1105              1110

Asp Pro  Pro Asn His Ala Arg  Ser Pro Gly Asn Lys  Gly Lys Gly
    1115              1120              1125

Lys Gly  Lys Gly Lys Gly Lys  Pro Lys Ser Gln Ala  Cys Glu Pro
    1130              1135              1140

Ser Glu  Pro Glu Ile Glu Ile  Lys Leu Pro Lys Leu  Arg Thr Leu
    1145              1150              1155

Asp Val  Phe Ser Gly Cys Gly  Gly Leu Ser Glu Gly  Phe His Gln
    1160              1165              1170

Ala Gly  Ile Ser Asp Thr Leu  Trp Ala Ile Glu Met  Trp Asp Pro
    1175              1180              1185

Ala Ala  Gln Ala Phe Arg Leu  Asn Asn Pro Gly Ser  Thr Val Phe
    1190              1195              1200

Thr Glu  Asp Cys Asn Ile Leu  Leu Lys Leu Val Met  Ala Gly Glu
    1205              1210              1215

Thr Thr  Asn Ser Arg Gly Gln  Arg Leu Pro Gln Lys  Gly Asp Val
    1220              1225              1230

Glu Met  Leu Cys Gly Gly Pro  Pro Cys Gln Gly Phe  Ser Gly Met
    1235              1240              1245

Asn Arg  Phe Asn Ser Arg Thr  Tyr Ser Lys Phe Lys  Asn Ser Leu
    1250              1255              1260

Val Val  Ser Phe Leu Ser Tyr  Cys Asp Tyr Tyr Arg  Pro Arg Phe
    1265              1270              1275

Phe Leu  Leu Glu Asn Val Arg  Asn Phe Val Ser Phe  Lys Arg Ser
    1280              1285              1290

Met Val  Leu Lys Leu Thr Leu  Arg Cys Leu Val Arg  Met Gly Tyr
    1295              1300              1305

Gln Cys  Thr Phe Gly Val Leu  Gln Ala Gly Gln Tyr  Gly Val Ala
    1310              1315              1320

Gln Thr  Arg Arg Arg Ala Ile  Ile Leu Ala Ala Ala  Pro Gly Glu
    1325              1330              1335

Lys Leu  Pro Leu Phe Pro Glu  Pro Leu His Val Phe  Ala Pro Arg
    1340              1345              1350

Ala Cys  Gln Leu Ser Val Val  Asp Asp Lys Lys  Phe Val Ser
    1355              1360              1365

Asn Ile  Thr Arg Leu Ser Ser  Gly Pro Phe Arg Thr  Ile Thr Val
    1370              1375              1380
```

```
Arg Asp Thr Met Ser Asp Leu Pro Glu Val Arg Asn Gly Ala Ser
    1385                1390                1395

Ala Leu Glu Ile Ser Tyr Asn Gly Glu Pro Gln Ser Trp Phe Gln
    1400                1405                1410

Arg Gln Leu Arg Gly Ala Gln Tyr Gln Pro Ile Leu Arg Asp His
    1415                1420                1425

Ile Cys Lys Asp Met Ser Ala Leu Val Ala Ala Arg Met Arg His
    1430                1435                1440

Ile Pro Leu Ala Pro Gly Ser Asp Trp Arg Asp Leu Pro Asn Ile
    1445                1450                1455

Glu Val Arg Leu Ser Asp Gly Thr Met Ala Arg Lys Leu Arg Tyr
    1460                1465                1470

Thr His His Asp Arg Lys Asn Gly Arg Ser Ser Gly Ala Leu
    1475                1480                1485

Arg Gly Val Cys Ser Cys Val Glu Ala Gly Lys Ala Cys Asp Pro
    1490                1495                1500

Ala Ala Arg Gln Phe Asn Thr Leu Ile Pro Trp Cys Leu Pro His
    1505                1510                1515

Thr Gly Asn Arg His Asn His Trp Ala Gly Leu Tyr Gly Arg Leu
    1520                1525                1530

Glu Trp Asp Gly Phe Phe Ser Thr Thr Val Thr Asn Pro Glu Pro
    1535                1540                1545

Met Gly Lys Gln Gly Arg Val Leu His Pro Glu Gln His Arg Val
    1550                1555                1560

Val Ser Val Arg Glu Cys Ala Arg Ser Gln Gly Phe Pro Asp Thr
    1565                1570                1575

Tyr Arg Leu Phe Gly Asn Ile Leu Asp Lys His Arg Gln Val Gly
    1580                1585                1590

Asn Ala Val Pro Pro Leu Ala Lys Ala Ile Gly Leu Glu Ile
    1595                1600                1605

Lys Leu Cys Met Leu Ala Lys Ala Arg Glu Ser Ala Ser Ala Lys
    1610                1615                1620

Ile Lys Glu Glu Glu Ala Ala Lys Asp
    1625                1630

<210> SEQ ID NO 5
<211> LENGTH: 1620
<212> TYPE: PRT
<213> ORGANISM: Mus musculus

<400> SEQUENCE: 5

Met Pro Ala Arg Thr Ala Pro Ala Arg Val Pro Ala Leu Ala Ser Pro
1               5                   10                  15

Ala Gly Ser Leu Pro Asp His Val Arg Arg Arg Leu Lys Asp Leu Glu
                20                  25                  30

Arg Asp Gly Leu Thr Glu Lys Glu Cys Val Arg Glu Lys Leu Asn Leu
        35                  40                  45

Leu His Glu Phe Leu Gln Thr Glu Ile Lys Ser Gln Leu Cys Asp Leu
    50                  55                  60

Glu Thr Lys Leu His Glu Glu Leu Ser Glu Gly Tyr Leu Ala
65                  70                  75                  80

Lys Val Lys Ser Leu Leu Asn Lys Asp Leu Ser Leu Glu Asn Gly Thr
                85                  90                  95

His Thr Leu Thr Gln Lys Ala Asn Gly Cys Pro Ala Asn Gly Ser Arg
```

```
                100             105             110
Pro Thr Trp Arg Ala Glu Met Ala Asp Ser Asn Arg Ser Pro Arg Ser
            115             120             125
Arg Pro Lys Pro Arg Gly Pro Arg Ser Lys Ser Asp Ser Asp Thr
130             135             140
Leu Ser Val Glu Thr Ser Pro Ser Ser Val Ala Thr Arg Arg Thr Thr
145             150             155             160
Arg Gln Thr Thr Ile Thr Ala His Phe Thr Lys Gly Pro Thr Lys Arg
                165             170             175
Lys Pro Lys Glu Glu Ser Glu Glu Gly Asn Ser Ala Glu Ser Ala Ala
            180             185             190
Glu Glu Arg Asp Gln Asp Lys Lys Arg Arg Val Val Asp Thr Glu Ser
            195             200             205
Gly Ala Ala Ala Val Glu Lys Leu Glu Glu Val Thr Ala Gly Thr
            210             215             220
Gln Leu Gly Pro Glu Glu Pro Cys Glu Gln Glu Asp Asp Asn Arg Ser
225             230             235             240
Leu Arg Arg His Thr Arg Glu Leu Ser Leu Arg Arg Lys Ser Lys Glu
                245             250             255
Asp Pro Asp Arg Glu Ala Arg Pro Glu Thr His Leu Asp Glu Asp Glu
            260             265             270
Asp Gly Lys Lys Asp Lys Arg Ser Ser Arg Pro Arg Ser Gln Pro Arg
            275             280             285
Asp Pro Ala Ala Lys Arg Arg Pro Lys Glu Ala Glu Pro Glu Gln Val
            290             295             300
Ala Pro Glu Thr Pro Glu Asp Arg Asp Glu Asp Glu Arg Glu Glu Lys
305             310             315             320
Arg Arg Lys Thr Thr Arg Lys Lys Leu Glu Ser His Thr Val Pro Val
                325             330             335
Gln Ser Arg Ser Glu Arg Lys Ala Ala Gln Ser Lys Ser Val Ile Pro
            340             345             350
Lys Ile Asn Ser Pro Lys Cys Pro Glu Cys Gly Gln His Leu Asp Asp
            355             360             365
Pro Asn Leu Lys Tyr Gln Gln His Pro Glu Asp Ala Val Asp Glu Pro
370             375             380
Gln Met Leu Thr Ser Glu Lys Leu Ser Ile Tyr Asp Ser Thr Ser Thr
385             390             395             400
Trp Phe Asp Thr Tyr Glu Asp Ser Pro Met His Arg Phe Thr Ser Phe
                405             410             415
Ser Val Tyr Cys Ser Arg Gly His Leu Cys Pro Val Asp Thr Gly Leu
            420             425             430
Ile Glu Lys Asn Val Glu Leu Tyr Phe Ser Gly Cys Ala Lys Ala Ile
            435             440             445
His Asp Glu Asn Pro Ser Met Glu Gly Gly Ile Asn Gly Lys Asn Leu
            450             455             460
Gly Pro Ile Asn Gln Trp Trp Leu Ser Gly Phe Asp Gly Gly Glu Lys
465             470             475             480
Val Leu Ile Gly Phe Ser Thr Ala Phe Ala Glu Tyr Ile Leu Met Glu
                485             490             495
Pro Ser Lys Glu Tyr Glu Pro Ile Phe Gly Leu Met Gln Glu Lys Ile
            500             505             510
Tyr Ile Ser Lys Ile Val Val Glu Phe Leu Gln Asn Asn Pro Asp Ala
            515             520             525
```

```
Val Tyr Glu Asp Leu Ile Asn Lys Ile Glu Thr Thr Val Pro Pro Ser
        530                 535                 540

Thr Ile Asn Val Asn Arg Phe Thr Glu Asp Ser Leu Leu Arg His Ala
545                 550                 555                 560

Gln Phe Val Val Ser Gln Val Glu Ser Tyr Asp Glu Ala Lys Asp Asp
                565                 570                 575

Asp Glu Thr Pro Ile Phe Leu Ser Pro Cys Met Arg Ala Leu Ile His
            580                 585                 590

Leu Ala Gly Val Ser Leu Gly Gln Arg Arg Ala Thr Arg Arg Val Met
        595                 600                 605

Gly Ala Thr Lys Glu Lys Asp Lys Ala Pro Thr Lys Ala Thr Thr Thr
610                 615                 620

Lys Leu Val Tyr Gln Ile Phe Asp Thr Phe Phe Ser Glu Gln Ile Glu
625                 630                 635                 640

Lys Tyr Asp Lys Glu Asp Lys Glu Asn Ala Met Lys Arg Arg Arg Cys
                645                 650                 655

Gly Val Cys Glu Val Cys Gln Gln Pro Glu Cys Gly Lys Cys Lys Ala
                660                 665                 670

Cys Lys Asp Met Val Lys Phe Gly Gly Thr Gly Arg Ser Lys Gln Ala
            675                 680                 685

Cys Leu Lys Arg Arg Cys Pro Asn Leu Ala Val Lys Glu Ala Asp Asp
690                 695                 700

Asp Glu Glu Ala Asp Asp Asp Val Ser Glu Met Pro Ser Pro Lys Lys
705                 710                 715                 720

Leu His Gln Gly Lys Lys Lys Gln Asn Lys Asp Arg Ile Ser Trp
                725                 730                 735

Leu Gly Gln Pro Met Lys Ile Glu Glu Asn Arg Thr Tyr Tyr Gln Lys
            740                 745                 750

Val Ser Ile Asp Glu Glu Met Leu Glu Val Gly Asp Cys Val Ser Val
        755                 760                 765

Ile Pro Asp Asp Ser Ser Lys Pro Leu Tyr Leu Ala Arg Val Thr Ala
770                 775                 780

Leu Trp Glu Asp Lys Asn Gly Gln Met Met Phe His Ala His Trp Phe
785                 790                 795                 800

Cys Ala Gly Thr Asp Thr Val Leu Gly Ala Thr Ser Asp Pro Leu Glu
                805                 810                 815

Leu Phe Leu Val Gly Glu Cys Glu Asn Met Gln Leu Ser Tyr Ile His
                820                 825                 830

Ser Lys Val Lys Val Ile Tyr Lys Ala Pro Ser Glu Asn Trp Ala Met
        835                 840                 845

Glu Gly Gly Thr Asp Pro Glu Thr Thr Leu Pro Gly Ala Glu Asp Gly
850                 855                 860

Lys Thr Tyr Phe Phe Gln Leu Trp Tyr Asn Gln Glu Tyr Ala Arg Phe
865                 870                 875                 880

Glu Ser Pro Pro Lys Thr Gln Pro Thr Glu Asp Asn Lys His Lys Phe
                885                 890                 895

Cys Leu Ser Cys Ile Arg Leu Ala Glu Leu Arg Gln Lys Glu Met Pro
                900                 905                 910

Lys Val Leu Glu Gln Ile Glu Glu Val Asp Gly Arg Val Tyr Cys Ser
            915                 920                 925

Ser Ile Thr Lys Asn Gly Val Val Tyr Arg Leu Gly Asp Ser Val Tyr
930                 935                 940
```

```
Leu Pro Pro Glu Ala Phe Thr Phe Asn Ile Lys Val Ala Ser Pro Val
945                 950                 955                 960

Lys Arg Pro Lys Lys Asp Pro Val Asn Glu Thr Leu Tyr Pro Glu His
                965                 970                 975

Tyr Arg Lys Tyr Ser Asp Tyr Ile Lys Gly Ser Asn Leu Asp Ala Pro
            980                 985                 990

Glu Pro Tyr Arg Ile Gly Arg Ile Lys Glu Ile His Cys Gly Lys Lys
        995                 1000                1005

Lys Gly Lys Val Asn Glu Ala Asp Ile Lys Leu Arg Leu Tyr Lys
    1010                1015                1020

Phe Tyr Arg Pro Glu Asn Thr His Arg Ser Tyr Asn Gly Ser Tyr
    1025                1030                1035

His Thr Asp Ile Asn Met Leu Tyr Trp Ser Asp Glu Glu Ala Val
    1040                1045                1050

Val Asn Phe Ser Asp Val Gln Gly Arg Cys Thr Val Glu Tyr Gly
    1055                1060                1065

Glu Asp Leu Leu Glu Ser Ile Gln Asp Tyr Ser Gln Gly Gly Pro
    1070                1075                1080

Asp Arg Phe Tyr Phe Leu Glu Ala Tyr Asn Ser Lys Thr Lys Asn
    1085                1090                1095

Phe Glu Asp Pro Pro Asn His Ala Arg Ser Pro Gly Asn Lys Gly
    1100                1105                1110

Lys Gly Lys Gly Lys Gly Lys Gly Lys Gly Lys His Gln Val Ser
    1115                1120                1125

Glu Pro Lys Glu Pro Glu Ala Ala Ile Lys Leu Pro Lys Leu Arg
    1130                1135                1140

Thr Leu Asp Val Phe Ser Gly Cys Gly Gly Leu Ser Glu Gly Phe
    1145                1150                1155

His Gln Ala Gly Ile Ser Glu Thr Leu Trp Ala Ile Glu Met Trp
    1160                1165                1170

Asp Pro Ala Ala Gln Ala Phe Arg Leu Asn Asn Pro Gly Thr Thr
    1175                1180                1185

Val Phe Thr Glu Asp Cys Asn Val Leu Leu Lys Leu Val Met Ala
    1190                1195                1200

Gly Glu Val Thr Asn Ser Leu Gly Gln Arg Leu Pro Gln Lys Gly
    1205                1210                1215

Asp Val Glu Met Leu Cys Gly Gly Pro Pro Cys Gln Gly Phe Ser
    1220                1225                1230

Gly Met Asn Arg Phe Asn Ser Arg Thr Tyr Ser Lys Phe Lys Asn
    1235                1240                1245

Ser Leu Val Val Ser Phe Leu Ser Tyr Cys Asp Tyr Tyr Arg Pro
    1250                1255                1260

Arg Phe Phe Leu Leu Glu Asn Val Arg Asn Phe Val Ser Tyr Arg
    1265                1270                1275

Arg Ser Met Val Leu Lys Leu Thr Leu Arg Cys Leu Val Arg Met
    1280                1285                1290

Gly Tyr Gln Cys Thr Phe Gly Val Leu Gln Ala Gly Gln Tyr Gly
    1295                1300                1305

Val Ala Gln Thr Arg Arg Arg Ala Ile Ile Leu Ala Ala Ala Pro
    1310                1315                1320

Gly Glu Lys Leu Pro Leu Phe Pro Glu Pro Leu His Val Phe Ala
    1325                1330                1335

Pro Arg Ala Cys Gln Leu Ser Val Val Val Asp Asp Lys Lys Phe
```

1340                1345                1350

Val Ser Asn Ile Thr Arg Leu Ser Ser Gly Pro Phe Arg Thr Ile
    1355                1360                1365

Thr Val Arg Asp Thr Met Ser Asp Leu Pro Glu Ile Gln Asn Gly
    1370                1375                1380

Ala Ser Asn Ser Glu Ile Pro Tyr Asn Gly Glu Pro Leu Ser Trp
    1385                1390                1395

Phe Gln Arg Gln Leu Arg Gly Ser His Tyr Gln Pro Ile Leu Arg
    1400                1405                1410

Asp His Ile Cys Lys Asp Met Ser Pro Leu Val Ala Ala Arg Met
    1415                1420                1425

Arg His Ile Pro Leu Phe Pro Gly Ser Asp Trp Arg Asp Leu Pro
    1430                1435                1440

Asn Ile Gln Val Arg Leu Gly Asp Gly Val Ile Ala His Lys Leu
    1445                1450                1455

Gln Tyr Thr Phe His Asp Val Lys Asn Gly Tyr Ser Ser Thr Gly
    1460                1465                1470

Ala Leu Arg Gly Val Cys Ser Cys Ala Glu Gly Lys Ala Cys Asp
    1475                1480                1485

Pro Glu Ser Arg Gln Phe Ser Thr Leu Ile Pro Trp Cys Leu Pro
    1490                1495                1500

His Thr Gly Asn Arg His Asn His Trp Ala Gly Leu Tyr Gly Arg
    1505                1510                1515

Leu Glu Trp Asp Gly Phe Phe Ser Thr Thr Val Thr Asn Pro Glu
    1520                1525                1530

Pro Met Gly Lys Gln Gly Arg Val Leu His Pro Glu Gln His Arg
    1535                1540                1545

Val Val Ser Val Arg Glu Cys Ala Arg Ser Gln Gly Phe Pro Asp
    1550                1555                1560

Ser Tyr Arg Phe Phe Gly Asn Ile Leu Asp Arg His Arg Gln Val
    1565                1570                1575

Gly Asn Ala Val Pro Pro Pro Leu Ala Lys Ala Ile Gly Leu Glu
    1580                1585                1590

Ile Lys Leu Cys Leu Leu Ser Ser Ala Arg Glu Ser Ala Ser Ala
    1595                1600                1605

Ala Val Lys Ala Lys Glu Glu Ala Ala Thr Lys Asp
    1610                1615                1620

<210> SEQ ID NO 6
<211> LENGTH: 912
<212> TYPE: PRT
<213> ORGANISM: Homo sapiens

<400> SEQUENCE: 6

Met Pro Ala Met Pro Ser Ser Gly Pro Gly Asp Thr Ser Ser Ala
1               5                   10                  15

Ala Glu Arg Glu Glu Asp Arg Lys Asp Gly Glu Glu Gln Glu Pro
                20                  25                  30

Arg Gly Lys Glu Glu Arg Gln Glu Pro Ser Thr Thr Ala Arg Lys Val
        35                  40                  45

Gly Arg Pro Gly Arg Lys Arg Lys His Pro Pro Val Glu Ser Gly Asp
    50                  55                  60

Thr Pro Lys Asp Pro Ala Val Ile Ser Lys Ser Pro Ser Met Ala Gln
65                  70                  75                  80

```
Asp Ser Gly Ala Ser Glu Leu Leu Pro Asn Gly Asp Leu Glu Lys Arg
            85                  90                  95

Ser Glu Pro Gln Pro Glu Glu Gly Ser Pro Ala Gly Gly Gln Lys Gly
        100                 105                 110

Gly Ala Pro Ala Glu Gly Glu Gly Ala Ala Glu Thr Leu Pro Glu Ala
        115                 120                 125

Ser Arg Ala Val Glu Asn Gly Cys Cys Thr Pro Lys Glu Gly Arg Gly
        130                 135                 140

Ala Pro Ala Glu Ala Gly Lys Glu Gln Lys Glu Thr Asn Ile Glu Ser
145                 150                 155                 160

Met Lys Met Glu Gly Ser Arg Gly Arg Leu Arg Gly Gly Leu Gly Trp
                165                 170                 175

Glu Ser Ser Leu Arg Gln Arg Pro Met Pro Arg Leu Thr Phe Gln Ala
                180                 185                 190

Gly Asp Pro Tyr Tyr Ile Ser Lys Arg Lys Arg Asp Glu Trp Leu Ala
            195                 200                 205

Arg Trp Lys Arg Glu Ala Glu Lys Lys Ala Lys Val Ile Ala Gly Met
            210                 215                 220

Asn Ala Val Glu Glu Asn Gln Gly Pro Gly Glu Ser Gln Lys Val Glu
225                 230                 235                 240

Glu Ala Ser Pro Pro Ala Val Gln Gln Pro Thr Asp Pro Ala Ser Pro
                245                 250                 255

Thr Val Ala Thr Thr Pro Glu Pro Val Gly Ser Asp Ala Gly Asp Lys
                260                 265                 270

Asn Ala Thr Lys Ala Gly Asp Asp Glu Pro Glu Tyr Glu Asp Gly Arg
            275                 280                 285

Gly Phe Gly Ile Gly Glu Leu Val Trp Gly Lys Leu Arg Gly Phe Ser
            290                 295                 300

Trp Trp Pro Gly Arg Ile Val Ser Trp Trp Met Thr Gly Arg Ser Arg
305                 310                 315                 320

Ala Ala Glu Gly Thr Arg Trp Val Met Trp Phe Gly Asp Gly Lys Phe
                325                 330                 335

Ser Val Val Cys Val Glu Lys Leu Met Pro Leu Ser Ser Phe Cys Ser
                340                 345                 350

Ala Phe His Gln Ala Thr Tyr Asn Lys Gln Pro Met Tyr Arg Lys Ala
            355                 360                 365

Ile Tyr Glu Val Leu Gln Val Ala Ser Ser Arg Ala Gly Lys Leu Phe
            370                 375                 380

Pro Val Cys His Asp Ser Asp Glu Ser Asp Thr Ala Lys Ala Val Glu
385                 390                 395                 400

Val Gln Asn Lys Pro Met Ile Glu Trp Ala Leu Gly Gly Phe Gln Pro
                405                 410                 415

Ser Gly Pro Lys Gly Leu Glu Pro Pro Glu Glu Glu Lys Asn Pro Tyr
            420                 425                 430

Lys Glu Val Tyr Thr Asp Met Trp Val Glu Pro Glu Ala Ala Ala Tyr
            435                 440                 445

Ala Pro Pro Pro Pro Ala Lys Lys Pro Arg Lys Ser Thr Ala Glu Lys
        450                 455                 460

Pro Lys Val Lys Glu Ile Ile Asp Glu Arg Thr Arg Glu Arg Leu Val
465                 470                 475                 480

Tyr Glu Val Arg Gln Lys Cys Arg Asn Ile Glu Asp Ile Cys Ile Ser
                485                 490                 495

Cys Gly Ser Leu Asn Val Thr Leu Glu His Pro Leu Phe Val Gly Gly
```

-continued

```
                500                 505                 510
Met Cys Gln Asn Cys Lys Asn Cys Phe Leu Glu Cys Ala Tyr Gln Tyr
            515                 520                 525

Asp Asp Asp Gly Tyr Gln Ser Tyr Cys Thr Ile Cys Cys Gly Gly Arg
        530                 535                 540

Glu Val Leu Met Cys Gly Asn Asn Asn Cys Arg Cys Phe Cys Val
545                 550                 555                 560

Glu Cys Val Asp Leu Leu Val Gly Pro Gly Ala Ala Gln Ala Ala Ile
                565                 570                 575

Lys Glu Asp Pro Trp Asn Cys Tyr Met Cys Gly His Lys Gly Thr Tyr
            580                 585                 590

Gly Leu Leu Arg Arg Arg Glu Asp Trp Pro Ser Arg Leu Gln Met Phe
        595                 600                 605

Phe Ala Asn Asn His Asp Gln Glu Phe Asp Pro Pro Lys Val Tyr Pro
            610                 615                 620

Pro Val Pro Ala Glu Lys Arg Lys Pro Ile Arg Val Leu Ser Leu Phe
625                 630                 635                 640

Asp Gly Ile Ala Thr Gly Leu Leu Val Leu Lys Asp Leu Gly Ile Gln
                645                 650                 655

Val Asp Arg Tyr Ile Ala Ser Glu Val Cys Glu Asp Ser Ile Thr Val
            660                 665                 670

Gly Met Val Arg His Gln Gly Lys Ile Met Tyr Val Gly Asp Val Arg
        675                 680                 685

Ser Val Thr Gln Lys His Ile Gln Glu Trp Gly Pro Phe Asp Leu Val
        690                 695                 700

Ile Gly Gly Ser Pro Cys Asn Asp Leu Ser Ile Val Asn Pro Ala Arg
705                 710                 715                 720

Lys Gly Leu Tyr Glu Gly Thr Gly Arg Leu Phe Phe Glu Phe Tyr Arg
                725                 730                 735

Leu Leu His Asp Ala Arg Pro Lys Glu Gly Asp Asp Arg Pro Phe Phe
            740                 745                 750

Trp Leu Phe Glu Asn Val Val Ala Met Gly Val Ser Asp Lys Arg Asp
        755                 760                 765

Ile Ser Arg Phe Leu Glu Ser Asn Pro Val Met Ile Asp Ala Lys Glu
        770                 775                 780

Val Ser Ala Ala His Arg Ala Arg Tyr Phe Trp Gly Asn Leu Pro Gly
785                 790                 795                 800

Met Asn Arg Pro Leu Ala Ser Thr Val Asn Asp Lys Leu Glu Leu Gln
                805                 810                 815

Glu Cys Leu Glu His Gly Arg Ile Ala Lys Phe Ser Lys Val Arg Thr
            820                 825                 830

Ile Thr Thr Arg Ser Asn Ser Ile Lys Gln Gly Lys Asp Gln His Phe
        835                 840                 845

Pro Val Phe Met Asn Glu Lys Glu Asp Ile Leu Trp Cys Thr Glu Met
        850                 855                 860

Glu Arg Val Phe Gly Phe Pro Val His Tyr Thr Asp Val Ser Asn Met
865                 870                 875                 880

Ser Arg Leu Ala Arg Gln Arg Leu Leu Gly Arg Ser Trp Ser Val Pro
                885                 890                 895

Val Ile Arg His Leu Phe Ala Pro Leu Lys Glu Tyr Phe Ala Cys Val
            900                 905                 910
```

<210> SEQ ID NO 7

<211> LENGTH: 908
<212> TYPE: PRT
<213> ORGANISM: Mus musculus

<400> SEQUENCE: 7

```
Met Pro Ser Ser Gly Pro Gly Asp Thr Ser Ser Ser Leu Glu Arg
1               5                   10                  15

Glu Asp Asp Arg Lys Glu Gly Glu Gln Glu Glu Asn Arg Gly Lys
            20                  25                  30

Glu Glu Arg Gln Glu Pro Ser Ala Thr Ala Arg Lys Val Gly Arg Pro
        35                  40                  45

Gly Arg Lys Arg Lys His Pro Pro Val Glu Ser Ser Asp Thr Pro Lys
50                  55                  60

Asp Pro Ala Val Thr Thr Lys Ser Gln Pro Met Ala Gln Asp Ser Gly
65                  70                  75                  80

Pro Ser Asp Leu Leu Pro Asn Gly Asp Leu Glu Lys Arg Ser Glu Pro
                85                  90                  95

Gln Pro Glu Glu Gly Ser Pro Ala Ala Gly Gln Lys Gly Gly Ala Pro
            100                 105                 110

Ala Glu Gly Glu Gly Thr Glu Thr Pro Pro Glu Ala Ser Arg Ala Val
        115                 120                 125

Glu Asn Gly Cys Cys Val Thr Lys Glu Gly Arg Gly Ala Ser Ala Gly
130                 135                 140

Glu Gly Lys Glu Gln Lys Gln Thr Asn Ile Glu Ser Met Lys Met Glu
145                 150                 155                 160

Gly Ser Arg Gly Arg Leu Arg Gly Gly Leu Gly Trp Glu Ser Ser Leu
                165                 170                 175

Arg Gln Arg Pro Met Pro Arg Leu Thr Phe Gln Ala Gly Asp Pro Tyr
            180                 185                 190

Tyr Ile Ser Lys Arg Lys Arg Asp Glu Trp Leu Ala Arg Trp Lys Arg
        195                 200                 205

Glu Ala Glu Lys Lys Ala Lys Val Ile Ala Val Met Asn Ala Val Glu
210                 215                 220

Glu Asn Gln Ala Ser Gly Glu Ser Gln Lys Val Glu Glu Ala Ser Pro
225                 230                 235                 240

Pro Ala Val Gln Gln Pro Thr Asp Pro Ala Ser Pro Thr Val Ala Thr
                245                 250                 255

Thr Pro Glu Pro Val Gly Gly Asp Ala Gly Asp Lys Asn Ala Thr Lys
            260                 265                 270

Ala Ala Asp Asp Glu Pro Glu Tyr Glu Asp Gly Arg Gly Phe Gly Ile
        275                 280                 285

Gly Glu Leu Val Trp Gly Lys Leu Arg Gly Phe Ser Trp Trp Pro Gly
290                 295                 300

Arg Ile Val Ser Trp Trp Met Thr Gly Arg Ser Arg Ala Ala Glu Gly
305                 310                 315                 320

Thr Arg Trp Val Met Trp Phe Gly Asp Gly Lys Phe Ser Val Val Cys
                325                 330                 335

Val Glu Lys Leu Met Pro Leu Ser Ser Phe Cys Ser Ala Phe His Gln
            340                 345                 350

Ala Thr Tyr Asn Lys Gln Pro Met Tyr Arg Lys Ala Ile Tyr Glu Val
        355                 360                 365

Leu Gln Val Ala Ser Ser Arg Ala Gly Lys Leu Phe Pro Ala Cys His
370                 375                 380

Asp Ser Asp Glu Ser Asp Ser Gly Lys Ala Val Glu Val Gln Asn Lys
```

-continued

```
            385                 390                 395                 400
        Gln Met Ile Glu Trp Ala Leu Gly Gly Phe Gln Pro Ser Gly Pro Lys
                        405                 410                 415
        Gly Leu Glu Pro Pro Glu Glu Lys Asn Pro Tyr Lys Glu Val Tyr
                        420                 425                 430
        Thr Asp Met Trp Val Glu Pro Ala Ala Tyr Ala Pro Pro Pro
                        435                 440                 445
        Pro Ala Lys Lys Pro Arg Lys Ser Thr Thr Glu Lys Pro Lys Val Lys
        450                 455                 460
        Glu Ile Ile Asp Glu Arg Thr Arg Glu Arg Leu Val Tyr Glu Val Arg
        465                 470                 475                 480
        Gln Lys Cys Arg Asn Ile Glu Asp Ile Cys Ile Ser Cys Gly Ser Leu
                        485                 490                 495
        Asn Val Thr Leu Glu His Pro Leu Phe Ile Gly Gly Met Cys Gln Asn
                        500                 505                 510
        Cys Lys Asn Cys Phe Leu Glu Cys Ala Tyr Gln Tyr Asp Asp Asp Gly
                        515                 520                 525
        Tyr Gln Ser Tyr Cys Thr Ile Cys Cys Gly Gly Arg Glu Val Leu Met
                        530                 535                 540
        Cys Gly Asn Asn Asn Cys Cys Arg Cys Phe Cys Val Glu Cys Val Asp
        545                 550                 555                 560
        Leu Leu Val Gly Pro Gly Ala Ala Gln Ala Ala Ile Lys Glu Asp Pro
                        565                 570                 575
        Trp Asn Cys Tyr Met Cys Gly His Lys Gly Thr Tyr Gly Leu Leu Arg
                        580                 585                 590
        Arg Arg Glu Asp Trp Pro Ser Arg Leu Gln Met Phe Phe Ala Asn Asn
                        595                 600                 605
        His Asp Gln Glu Phe Asp Pro Pro Lys Val Tyr Pro Pro Val Pro Ala
                        610                 615                 620
        Glu Lys Arg Lys Pro Ile Arg Val Leu Ser Leu Phe Asp Gly Ile Ala
        625                 630                 635                 640
        Thr Gly Leu Leu Val Leu Lys Asp Leu Gly Ile Gln Val Asp Arg Tyr
                        645                 650                 655
        Ile Ala Ser Glu Val Cys Glu Asp Ser Ile Thr Val Gly Met Val Arg
                        660                 665                 670
        His Gln Gly Lys Ile Met Tyr Val Gly Asp Val Arg Ser Val Thr Gln
                        675                 680                 685
        Lys His Ile Gln Glu Trp Gly Pro Phe Asp Leu Val Ile Gly Gly Ser
                        690                 695                 700
        Pro Cys Asn Asp Leu Ser Ile Val Asn Pro Ala Arg Lys Gly Leu Tyr
        705                 710                 715                 720
        Glu Gly Thr Gly Arg Leu Phe Phe Glu Phe Tyr Arg Leu Leu His Asp
                        725                 730                 735
        Ala Arg Pro Lys Glu Gly Asp Asp Arg Pro Phe Phe Trp Leu Phe Glu
                        740                 745                 750
        Asn Val Val Ala Met Gly Val Ser Asp Lys Arg Asp Ile Ser Arg Phe
                        755                 760                 765
        Leu Glu Ser Asn Pro Val Met Ile Asp Ala Lys Glu Val Ser Ala Ala
                        770                 775                 780
        His Arg Ala Arg Tyr Phe Trp Gly Asn Leu Pro Gly Met Asn Arg Pro
        785                 790                 795                 800
        Leu Ala Ser Thr Val Asn Asp Lys Leu Glu Leu Gln Glu Cys Leu Glu
                        805                 810                 815
```

```
His Gly Arg Ile Ala Lys Phe Ser Lys Val Arg Thr Ile Thr Thr Arg
            820                 825                 830

Ser Asn Ser Ile Lys Gln Gly Lys Asp Gln His Phe Pro Val Phe Met
        835                 840                 845

Asn Glu Lys Glu Asp Ile Leu Trp Cys Thr Glu Met Glu Arg Val Phe
850                 855                 860

Gly Phe Pro Val His Tyr Thr Asp Val Ser Asn Met Ser Arg Leu Ala
865                 870                 875                 880

Arg Gln Arg Leu Leu Gly Arg Ser Trp Ser Val Pro Val Ile Arg His
                885                 890                 895

Leu Phe Ala Pro Leu Lys Glu Tyr Phe Ala Cys Val
            900                 905

<210> SEQ ID NO 8
<211> LENGTH: 853
<212> TYPE: PRT
<213> ORGANISM: Homo sapiens

<400> SEQUENCE: 8

Met Lys Gly Asp Thr Arg His Leu Asn Gly Glu Glu Asp Ala Gly Gly
1               5                   10                  15

Arg Glu Asp Ser Ile Leu Val Asn Gly Ala Cys Ser Asp Gln Ser Ser
            20                  25                  30

Asp Ser Pro Pro Ile Leu Glu Ala Ile Arg Thr Pro Glu Ile Arg Gly
        35                  40                  45

Arg Arg Ser Ser Ser Arg Leu Ser Lys Arg Glu Val Ser Ser Leu Leu
    50                  55                  60

Ser Tyr Thr Gln Asp Leu Thr Gly Asp Gly Asp Gly Glu Asp Gly Asp
65              70                  75                  80

Gly Ser Asp Thr Pro Val Met Pro Lys Leu Phe Arg Glu Thr Arg Thr
                85                  90                  95

Arg Ser Glu Ser Pro Ala Val Arg Thr Arg Asn Asn Asn Ser Val Ser
            100                 105                 110

Ser Arg Glu Arg His Arg Pro Ser Pro Arg Ser Thr Arg Gly Arg Gln
        115                 120                 125

Gly Arg Asn His Val Asp Glu Ser Pro Val Glu Phe Pro Ala Thr Arg
    130                 135                 140

Ser Leu Arg Arg Arg Ala Thr Ala Ser Ala Gly Thr Pro Trp Pro Ser
145                 150                 155                 160

Pro Pro Ser Ser Tyr Leu Thr Ile Asp Leu Thr Asp Asp Thr Glu Asp
                165                 170                 175

Thr His Gly Thr Pro Gln Ser Ser Ser Thr Pro Tyr Ala Arg Leu Ala
            180                 185                 190

Gln Asp Ser Gln Gln Gly Gly Met Glu Ser Pro Gln Val Glu Ala Asp
        195                 200                 205

Ser Gly Asp Gly Asp Ser Glu Tyr Gln Asp Gly Lys Glu Phe Gly
    210                 215                 220

Ile Gly Asp Leu Val Trp Gly Lys Ile Lys Gly Phe Ser Trp Trp Pro
225                 230                 235                 240

Ala Met Val Val Ser Trp Lys Ala Thr Ser Lys Arg Gln Ala Met Ser
                245                 250                 255

Gly Met Arg Trp Val Gln Trp Phe Gly Asp Gly Lys Phe Ser Glu Val
            260                 265                 270

Ser Ala Asp Lys Leu Val Ala Leu Gly Leu Phe Ser Gln His Phe Asn
```

-continued

```
                275                 280                 285
Leu Ala Thr Phe Asn Lys Leu Val Ser Tyr Arg Lys Ala Met Tyr His
290                 295                 300
Ala Leu Glu Lys Ala Arg Val Arg Ala Gly Lys Thr Phe Pro Ser Ser
305                 310                 315                 320
Pro Gly Asp Ser Leu Glu Asp Gln Leu Lys Pro Met Leu Glu Trp Ala
                325                 330                 335
His Gly Gly Phe Lys Pro Thr Gly Ile Glu Gly Leu Lys Pro Asn Asn
                340                 345                 350
Thr Gln Pro Val Val Asn Lys Ser Lys Val Arg Arg Ala Gly Ser Arg
                355                 360                 365
Lys Leu Glu Ser Arg Lys Tyr Glu Asn Lys Thr Arg Arg Thr Ala
370                 375                 380
Asp Asp Ser Ala Thr Ser Asp Tyr Cys Pro Ala Pro Lys Arg Leu Lys
385                 390                 395                 400
Thr Asn Cys Tyr Asn Asn Gly Lys Asp Arg Gly Asp Glu Asp Gln Ser
                405                 410                 415
Arg Glu Gln Met Ala Ser Asp Val Ala Asn Asn Lys Ser Ser Leu Glu
                420                 425                 430
Asp Gly Cys Leu Ser Cys Gly Arg Lys Asn Pro Val Ser Phe His Pro
                435                 440                 445
Leu Phe Glu Gly Gly Leu Cys Gln Thr Cys Arg Asp Arg Phe Leu Glu
450                 455                 460
Leu Phe Tyr Met Tyr Asp Asp Gly Tyr Gln Ser Tyr Cys Thr Val
465                 470                 475                 480
Cys Cys Glu Gly Arg Glu Leu Leu Cys Ser Asn Thr Ser Cys Cys
                485                 490                 495
Arg Cys Phe Cys Val Glu Cys Leu Glu Val Leu Val Gly Thr Gly Thr
                500                 505                 510
Ala Ala Glu Ala Lys Leu Gln Glu Pro Trp Ser Cys Tyr Met Cys Leu
                515                 520                 525
Pro Gln Arg Cys His Gly Val Leu Arg Arg Lys Asp Trp Asn Val
530                 535                 540
Arg Leu Gln Ala Phe Phe Thr Ser Asp Thr Gly Leu Glu Tyr Glu Ala
545                 550                 555                 560
Pro Lys Leu Tyr Pro Ala Ile Pro Ala Ala Arg Arg Arg Pro Ile Arg
                565                 570                 575
Val Leu Ser Leu Phe Asp Gly Ile Ala Thr Gly Tyr Leu Val Leu Lys
                580                 585                 590
Glu Leu Gly Ile Lys Val Gly Lys Tyr Val Ala Ser Glu Val Cys Glu
                595                 600                 605
Glu Ser Ile Ala Val Gly Thr Val Lys His Glu Gly Asn Ile Lys Tyr
                610                 615                 620
Val Asn Asp Val Arg Asn Ile Thr Lys Lys Asn Ile Glu Glu Trp Gly
625                 630                 635                 640
Pro Phe Asp Leu Val Ile Gly Gly Ser Pro Cys Asn Asp Leu Ser Asn
                645                 650                 655
Val Asn Pro Ala Arg Lys Gly Leu Tyr Glu Gly Thr Gly Arg Leu Phe
                660                 665                 670
Phe Glu Phe Tyr His Leu Leu Asn Tyr Ser Arg Pro Lys Glu Gly Asp
                675                 680                 685
Asp Arg Pro Phe Phe Trp Met Phe Glu Asn Val Val Ala Met Lys Val
                690                 695                 700
```

```
Gly Asp Lys Arg Asp Ile Ser Arg Phe Leu Glu Cys Asn Pro Val Met
705                 710                 715                 720

Ile Asp Ala Ile Lys Val Ser Ala Ala His Arg Ala Arg Tyr Phe Trp
            725                 730                 735

Gly Asn Leu Pro Gly Met Asn Arg Pro Val Ile Ala Ser Lys Asn Asp
        740                 745                 750

Lys Leu Glu Leu Gln Asp Cys Leu Glu Tyr Asn Arg Ile Ala Lys Leu
    755                 760                 765

Lys Lys Val Gln Thr Ile Thr Thr Lys Ser Asn Ser Ile Lys Gln Gly
770                 775                 780

Lys Asn Gln Leu Phe Pro Val Val Met Asn Gly Lys Glu Asp Val Leu
785                 790                 795                 800

Trp Cys Thr Glu Leu Glu Arg Ile Phe Gly Phe Pro Val His Tyr Thr
            805                 810                 815

Asp Val Ser Asn Met Gly Arg Gly Ala Arg Gln Lys Leu Leu Gly Arg
        820                 825                 830

Ser Trp Ser Val Pro Val Ile Arg His Leu Phe Ala Pro Leu Lys Asp
    835                 840                 845

Tyr Phe Ala Cys Glu
    850

<210> SEQ ID NO 9
<211> LENGTH: 859
<212> TYPE: PRT
<213> ORGANISM: Mus musculus

<400> SEQUENCE: 9

Met Lys Gly Asp Ser Arg His Leu Asn Glu Glu Gly Ala Ser Gly
1               5                   10                  15

Tyr Glu Glu Cys Ile Ile Val Asn Gly Asn Phe Ser Asp Gln Ser Ser
            20                  25                  30

Asp Thr Lys Asp Ala Pro Ser Pro Val Leu Glu Ala Ile Cys Thr
        35                  40                  45

Glu Pro Val Cys Thr Pro Glu Thr Arg Gly Arg Arg Ser Ser Ser Arg
50                  55                  60

Leu Ser Lys Arg Glu Val Ser Ser Leu Leu Asn Tyr Thr Gln Asp Met
65                  70                  75                  80

Thr Gly Asp Gly Asp Arg Asp Asp Glu Val Asp Asp Gly Asn Gly Ser
            85                  90                  95

Asp Ile Leu Met Pro Lys Leu Thr Arg Glu Thr Lys Asp Thr Arg Thr
        100                 105                 110

Arg Ser Glu Ser Pro Ala Val Arg Thr Arg His Ser Asn Gly Thr Ser
    115                 120                 125

Ser Leu Glu Arg Gln Arg Ala Ser Pro Arg Ile Thr Arg Gly Arg Gln
130                 135                 140

Gly Arg His His Val Gln Glu Tyr Pro Val Glu Phe Pro Ala Thr Arg
145                 150                 155                 160

Ser Arg Arg Arg Arg Ala Ser Ser Ser Ala Ser Thr Pro Trp Ser Ser
            165                 170                 175

Pro Ala Ser Val Asp Phe Met Glu Glu Val Thr Pro Lys Ser Val Ser
        180                 185                 190

Thr Pro Ser Val Asp Leu Ser Gln Asp Gly Asp Gln Glu Gly Met Asp
    195                 200                 205

Thr Thr Gln Val Asp Ala Glu Ser Arg Asp Gly Asp Ser Thr Glu Tyr
```

-continued

```
            210                 215                 220
Gln Asp Asp Lys Glu Phe Gly Ile Gly Asp Leu Val Trp Gly Lys Ile
225                 230                 235                 240

Lys Gly Phe Ser Trp Pro Ala Met Val Ser Trp Lys Ala Thr
                245                 250                 255

Ser Lys Arg Gln Ala Met Pro Gly Met Arg Trp Val Gln Trp Phe Gly
                260                 265                 270

Asp Gly Lys Phe Ser Glu Ile Ser Ala Asp Lys Leu Val Ala Leu Gly
                275                 280                 285

Leu Phe Ser Gln His Phe Asn Leu Ala Thr Phe Asn Lys Leu Val Ser
    290                 295                 300

Tyr Arg Lys Ala Met Tyr His Thr Leu Glu Lys Ala Arg Val Arg Ala
305                 310                 315                 320

Gly Lys Thr Phe Ser Ser Pro Gly Glu Ser Leu Glu Asp Gln Leu
                325                 330                 335

Lys Pro Met Leu Glu Trp Ala His Gly Gly Phe Lys Pro Thr Gly Ile
                340                 345                 350

Glu Gly Leu Lys Pro Asn Lys Lys Gln Pro Val Val Asn Lys Ser Lys
                355                 360                 365

Val Arg Arg Ser Asp Ser Arg Asn Leu Glu Pro Arg Arg Glu Asn
    370                 375                 380

Lys Ser Arg Arg Arg Thr Thr Asn Asp Ser Ala Ala Ser Glu Ser Pro
385                 390                 395                 400

Pro Pro Lys Arg Leu Lys Thr Asn Ser Tyr Gly Gly Lys Asp Arg Gly
                405                 410                 415

Glu Asp Glu Glu Ser Arg Glu Arg Met Ala Ser Glu Val Thr Asn Asn
                420                 425                 430

Lys Gly Asn Leu Glu Asp Arg Cys Leu Ser Cys Gly Lys Lys Asn Pro
                435                 440                 445

Val Ser Phe His Pro Leu Phe Glu Gly Gly Leu Cys Gln Ser Cys Arg
    450                 455                 460

Asp Arg Phe Leu Glu Leu Phe Tyr Met Tyr Asp Glu Asp Gly Tyr Gln
465                 470                 475                 480

Ser Tyr Cys Thr Val Cys Cys Glu Gly Arg Glu Leu Leu Leu Cys Ser
                485                 490                 495

Asn Thr Ser Cys Cys Arg Cys Phe Cys Val Glu Cys Leu Glu Val Leu
                500                 505                 510

Val Gly Ala Gly Thr Ala Glu Asp Ala Lys Leu Gln Glu Pro Trp Ser
                515                 520                 525

Cys Tyr Met Cys Leu Pro Gln Arg Cys His Gly Val Leu Arg Arg Arg
                530                 535                 540

Lys Asp Trp Asn Met Arg Leu Gln Asp Phe Phe Thr Thr Asp Pro Asp
545                 550                 555                 560

Leu Glu Glu Phe Glu Pro Pro Lys Leu Tyr Pro Ala Ile Pro Ala Ala
                565                 570                 575

Lys Arg Arg Pro Ile Arg Val Leu Ser Leu Phe Asp Gly Ile Ala Thr
                580                 585                 590

Gly Tyr Leu Val Leu Lys Glu Leu Gly Ile Lys Val Glu Lys Tyr Ile
                595                 600                 605

Ala Ser Glu Val Cys Ala Glu Ser Ile Ala Val Gly Thr Val Lys His
    610                 615                 620

Glu Gly Gln Ile Lys Tyr Val Asn Asp Val Arg Lys Ile Thr Lys Lys
625                 630                 635                 640
```

```
Asn Ile Glu Glu Trp Gly Pro Phe Asp Leu Val Ile Gly Gly Ser Pro
                645             650             655
Cys Asn Asp Leu Ser Asn Val Asn Pro Ala Arg Lys Gly Leu Tyr Glu
            660             665             670
Gly Thr Gly Arg Leu Phe Phe Glu Phe Tyr His Leu Leu Asn Tyr Thr
        675             680             685
Arg Pro Lys Glu Gly Asp Asn Arg Pro Phe Phe Trp Met Phe Glu Asn
    690             695             700
Val Val Ala Met Lys Val Asn Asp Lys Lys Asp Ile Ser Arg Phe Leu
705             710             715             720
Ala Cys Asn Pro Val Met Ile Asp Ala Ile Lys Val Ser Ala Ala His
            725             730             735
Arg Ala Arg Tyr Phe Trp Gly Asn Leu Pro Gly Met Asn Arg Pro Val
        740             745             750
Met Ala Ser Lys Asn Asp Lys Leu Glu Leu Gln Asp Cys Leu Glu Phe
        755             760             765
Ser Arg Thr Ala Lys Leu Lys Lys Val Gln Thr Ile Thr Thr Lys Ser
    770             775             780
Asn Ser Ile Arg Gln Gly Lys Asn Gln Leu Phe Pro Val Val Met Asn
785             790             795             800
Gly Lys Asp Asp Val Leu Trp Cys Thr Glu Leu Glu Arg Ile Phe Gly
            805             810             815
Phe Pro Ala His Tyr Thr Asp Val Ser Asn Met Gly Arg Gly Ala Arg
            820             825             830
Gln Lys Leu Leu Gly Arg Ser Trp Ser Val Pro Val Ile Arg His Leu
        835             840             845
Phe Ala Pro Leu Lys Asp Tyr Phe Ala Cys Glu
    850             855
```

DNA 5-METHYL CYTOSINE DEMETHYLATION ACTIVITY OF VERTEBRATE DNA METHYLTRANSFERASES

REFERENCE TO RELATED APPLICATION

This application is a national stage application (under 35 U.S.C. 371) of PCT/US2013/074141 filed on Dec. 10, 2013, which claims priority to U.S. provisional application 61/736,180 filed on Dec. 12, 2012, all of which are herein incorporated by reference in their entireties.

FIELD OF THE INVENTION

The present invention relates generally to DNA demethylation activity of DNA methyltransferases, therapeutic and diagnostic uses thereof.

BACKGROUND OF THE INVENTION

In vertebrates, DNA methylation occurs primarily at the 5-position of cytosine (C) in CpG dyads and their genomic methylation patterns are established/maintained by the DNA (C-5)-methyltransferases, or DNMTs. Of the known vertebrate DNMTs, DNMT1 shows a substrates preference for hemi-methylated DNA and maintains the methylation patterns during DNA replication. DNMT3A and DNMT3B show equal C-5 methylation activities toward unmethylated and hemi-methylated DNA in vitro, and they are essential for de novo genomic DNA methylation as well development of the early embryos. The vertebrate DNA methylation system comprising the above three essential DNMTs is indispensable for the establishment of the genomic DNA methylation patterns, globally and locally, and consequently the processes of gene expression, neuroplasticity, differentiation, carcinogenesis, imprinting, X-inactivation and development.

It has remained elusive in literature before 2012 whether there exists enzyme(s) in vertebrates that could actively and directly convert 5-mC on DNA into C.

SUMMARY OF THE INVENTION

In one aspect, the invention relates to a method for identifying a test agent (or a compound) as a modulator of the active DNA demethylation activity of a DNA methyltransferase. The method comprises:
a) providing a methylated DNA;
b) providing a DNA methyltransferase;
c) allowing the methylated DNA to react with the DNA methyltransferase for a sufficient time to perform a demethylation reaction and generate a demethylated DNA product in the presence or absence of a test agent;
d) analyzing the extent of demethylation; and
d) comparing the extents of the demethylation in the presence and absence of the test agent, and thereby identify the test agent as a modulator of the DNA demethylation activity of the DNA methyltransferase;
wherein the test agent is identified as an inhibitor of the active DNA demethylation activity of the DNA methyltransferase when the extent of the demethylation is less in the presence of the test agent; or the test agent is identified as a stimulator of the active DNA demethylation activity of the DNA methyltransferase when the extent of demethylation is more in the presence of the test agent.

In one embodiment of the invention, the analyzing step is performed by a technique selected from the group consisting of a restriction digestion-polymer chain reaction (PCR) assay, a hydrolysis-thin layer chromatography assay, an antibody-based analysis, scintillation counting, autoradiography, dot blotting, a liquid chromatography-based analysis, and a Na bisulfite-based analysis.

In another embodiment of the invention, the demethylation reaction occurs in the presence of a calcium ion concentration of around 10 μM to 10 mM.

In another embodiment of the invention, the DNA methyltransferase is an isolated vertebrate DNA methyltransferase, or a recombinant DNA methyltransferase, or is present in a nuclear extract or is present in a cellular extract. The vertebrate DNA methyltransferase, the nuclear extract, or the cellular extract may be prepared from cells selected from the group consisting, of vertebrate cell cultures, vertebrate tissues, insect cells, worm cells, insect tissues, worm tissues, plant cells, plant tissues, yeast cells, and bacterial cells. The nuclear extract may be a sperm extract.

In another embodiment of the invention, the methylated DNA comprises a labeled methyl group. The methyl group in the methylated DNA may be radioactive-labeled.

In another embodiment of the invention, the aforementioned method steps (a) to (d) possess the following technical features: wherein:
(a) the methylated DNA provided in step (a) is a methylated reporter gene operably linked to a constitutive promoter and is present in a cell;
(b) the DNA methyltransferase provided in step (b) is operably linked to a constitutive promoter and is also present in the cell, or is endogenously present in the cell as an endogenous DNA methyltransferase;
(c) the demethylated DNA product generated in step (c) is a demethylated reporter gene, which expresses a reporter protein in the cell.
(d) the analyzing step is performed by a technique selected from the group consisting of:
 (i) analyzing the signal of the reporter protein encoded by the demethylated reporter gene in the cell;
 (ii) analyzing the reporter protein expression by Western blot; and
 (iii) isolating the methylated and demethylated reporter gene and analyzing the extent of demethylation by a restriction digestion-polymer chain reaction (PCR) assay, a hydrolysis-thin layer chromatography assay, an antibody-based analysis, scintillation counting, autoradiography, dot blotting, a liquid chromatography-based analysis, or a Na bisulfite-based analysis.

In one embodiment of the invention, the methylated reporter gene and the DNA methyltransferase are present in the cell via transfection. Alternatively, the DNA methyltransferase is an endogenous enzyme present in the cell.

The cell is transfected with the methylated reporter gene, and the DNA methyltransferase may be an exogenouse enzyme transfected into the same cell, or may be an endogenous enzyme already present in the same cell. In one embodiment, the methylated reporter gene and the DNA methyltransferase are co-transfected into the cell.

In one embodiment of the invention, the test agent is introduced into the cell or added to a culture medium bathing the cell.

In another embodiment of the invention, the methylated reporter gene comprises a DNA sequence of a gene selected from the group consisting of a fluorescent protein-encoding gene, a luciferase gene, a drug-resistant gene, and genes of cell survivals.

In another embodiment of the invention, the methylated DNA comprises 5-methylcytosine (5mC)-containing DNA.

In another embodiment of the invention, step (c) is performed under a condition that is free of a reducing agent or under a non-reducing condition.

The DNA methyltransferase may be a modified form of a wild-type DNA methyltransferase, said modified form retaining the active DNA demethylation activity of the wild-type DNA methyltransferase.

The DNA methyltransferase may be selected from the group consisting of DNA methyltransferase 1, DNA methyltransferase 3A, DNA methyltransferase 3B, and any combination thereof.

The constitutive promoter may be, but not limited to, a cytomegalovirus promoter.

In another aspect, the invention relates to a method for identifying a test agent as a modulator of the active DNA demethylation activity of a DNA methyltransferase, in which the method comprises:

(I)
- a) admixing a first composition comprising a methylated DNA with a second composition comprising the DNA methyltransferase in the presence or absence of a test agent;
- b) allowing a demethylation reaction to occur by reacting the methylated DNA with the DNA methyltransferase for a sufficient time to generate a demethylated DNA product;
- c) analyzing the extent of demethylation; and
- d) comparing the extents of the demethylation in the presence and absence of the test agent, and thereby identify the test agent for modulating active DNA demethylation activity of the DNA methyltransferase;
  wherein the test agent is identified as an inhibitor of the active DNA demethylation activity of the DNA methyltransferase when the extent of the demethylation is less in the presence of the test agent; or the test agent is identified as a stimulator of the active DNA demethylation activity of the DNA methyltransferase when the extent of demethylation is more in the presence of the test agent;

or (II)
1) providing a cell culture medium containing cells transfected with a reporter gene that is methylated and operably linked to a constitutive promoter, said cells containing an endogenous DNA methyltransferase or exogenously expressing a wild-type, a modified or a genetically engineered DNA methyltransferase;
2) exposing the cells to a test agent;
3) allowing a demethylation reaction to occur to generate a demethylated reporter gene, which expresses a reporter protein in the cells; and
4) analyzing the extent of demethylation of the reporter gene by examining the signal intensity of the reporter protein expressed by the demethylated reporter gene in the cells;
5) comparing the extents of the demethylation of the reporter gene in the presence and absence of the test agent, and thereby identify the test agent as a modulator of the DNA demethylation activity of the DNA methyltransferase;
wherein the test agent is identified as an inhibitor of the active DNA demethylation activity of the DNA methyltransferase when the extent of the demethylation is less in the presence of the test agent; or the test agent is identified as a stimulator of the active DNA demethylation activity of the DNA methyltransferase when the extent of demethylation is more in the presence of the test agent.

The wild-type DNA methyltransferase may be selected from the group consisting of DNA methyltransferase 1, DNA methyltransferase 3A, and DNA methyltransferase 3B.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 1 shows DNA 5-mC demethylation activities of the mammalian DNMTs. The 5-mC-containing DNA substrates were subjected to incubation in 293T nuclear extracts in buffer B with 10 mM $CaCl_2$ that contained the exogenously expressed EGFP (lanes 1 and 2), mouse DNMT1 (lanes 3 and 4), DNMT3A (lanes 5 and 6), DNMT3B (lanes 7 and 8), and their site-directed mutants (lanes 9-14), respectively. The extents of conversion of 5-mC to C were analyzed by hydrolysis-TLC assay and quantitatively shown in the histogram. The amounts of the exogenous wild type enzyme in lanes 4, 6, and 8 were similar to those of the mutant enzymes in lanes 10, 12, and 14, respectively (Western blotting data not shown). M, mock control without incubation; R, with incubation. Error bars indicate S.D.*, $p<0.05$ by t-test comparing bars 4, 6, and 8 to bar 2.

FIG. 2A shows calcium-dependence of the DNA 5-mC demethylation activities of recombinant DNMTs. Hydrolysis-TLC assay of conversion of 5-mC to C by recombinant DNMT3B. The DNA demethylation activity of the recombinant mouse DNMT3B was assayed by incubation of 40 nM 5-mC containing DNA substrate with 40 nM of the enzyme in buffer B containing 100 μg/ml BSA and increasing concentrations (0, 10 μM, 100 μM, 1 mM, 5 mM and 10 mM) of $CaCl_2$. The incubations were all at 37° C. for 4 h. The quantitative results are presented in the histogram. M, mock control without incubation. Error bars indicate S.D.*, $p<0.05$;**, $p<0.01$ by t-test comparing bars 3-7 to bar 2.

FIG. 2B shows a comparison of the DNA demethylation activities of recombinant hDNMT1, hDNMT3A and DNMT3B by hydrolysis-TLC assay. The 5-mC containing substrate was incubated at 37° C. for 4 h with 40 nM of each of the recombinant hDNMT1 (lane 2), hDNMT3A (lane 3) and DNMT3B (lane 4) in buffer B containing 100 μg/ml BSA and 1 mM of $CaCl_2$, and then analyzed by hydrolysis-TLC assay. The quantitative analysis is presented in the histogram. M, mock control without incubation; R, with incubation. Error bars indicate S.D.*, $p<0.05$;***, $p<0.005$ by t-test comparing bars 2-4 to bar 1.

FIG. 3A: The 5-mC containing DNA substrate was subjected to the demethylation reactions with 40 nM recombinant DNMT3B in buffer B containing 100 μg/ml BSA with or without the inclusion of 1 mM $CaCl_2$, 5 mM DTT, or 160 μM SAM. After incubation at 37° C. for 4 h, the DNA products were analyzed by the hydrolysis-TLC assay. The results are quantitatively presented in the histogram. Error bars indicate S.D.*, $p<0.05$ by t-test comparing bars 2-4 to bar 1. FIG. 3B: Unmethylated pMR1-8 plasmid DNA was incubated with 40 nM recombinant DNMT3B in buffer B containing 100 μg/ml BSA with or without 1 mM $CaCl_2$, 5 mM DTT, or 160 μM SAM. After incubation at 37° C. for 4 h, the extents of C methylation of the DNAs from the different reactions were determined by hydrolysis-TLC assay and quantitatively compared in the histogram. Error bars indicate S.D.

FIG. 4A: Strategy of a series of reactions testing the reversibility of DNA demethylation and methylation (see text for more details). Briefly, 5-mC containing DNA substrate was incubated at 37° C. for 2 h with 40 nM recombinant DNMT3B in buffer B containing 100 µg/ml BSA and 1 mM $CaCl_2$ (reaction 1). Then, 160 µM SAM were added and the incubation was continued for another 1 h (reaction 2). Finally, 1 mM $H_2O_2$ was added to the reaction mixture and the incubation continued for another 2 h (reaction 3). Rx, reactions. FIG. 4B: The DNA products from the 3 reactions outlined in 4A were purified and analyzed by hydrolysis-TLC assay. The data are quantitatively compared in the histogram. M, mock control without incubation. Error bars indicate S.D., *, $p<0.05$; ***, $p<0.005$.

FIG. 5A: Schematic diagram illustrating the stepwise processes of restriction digestion-PCR assay. This assay was used to estimate the extents of demethylation of methylated plasmid upon incubation with the porcine sperm nuclear extract under different conditions (FIG. 6). 20 ng of the 5-mC containing plasmid pMR1-8, with or without DNA demethylation reactions in the sperm nuclear extract, was digested by HpaII overnight at 37° C., and purified with Qiaquick Nucleotide Removal Kit (Qiagen). The proportion of HpaII-insensitive DNA substrate was analyzed by 12-15 cycles of PCR using a primer set bracketing the HpaII restriction cutting sites followed by the gel electrophoresis. The band intensities were further quantitatively estimated and compared. FIG. 5B: Schematic diagram illustrating the stepwise processes of hydrolysis-TLC assay. The double-stranded DNA substrates were digested by MspI at 37° C. overnight, and then dephosphorylated with calf intestine phosphatase (New England Biolabs) followed by purification by Qiaquick Nucleotide Removal Kit (Qiagen). The purified DNAs were end-labeled by using $\gamma^{32}P$-ATP and T4 polynucleotide kinase (New England Biolabs), and then digested by snake venom phosphodiesterase (Worthington) and DNaseI (Roche) overnight. The hydrolyzates were loaded onto PEI cellulose plates (Merck) and separated in the buffer isobutyric acid:water:ammonia (66:18:3) for 16-18 h. Autoradiography of the plates was carried out and the signals on the plates were quantitated using the Alpha Imaging, 2200 (Alpha Innotech Crop.).

FIG. 6A: Fully methylated plasmid DNA pMR1-8 was incubated at 37° C. for 2 h in the porcine sperm nuclear extract: with increasing concentrations (0, 10 µM, 100 µM, 1 mM and 10 mM) of $CaCl_2$ (lanes 1-5), $MgCl_2$ (lanes 6-10) or $Fe(NH_4SO_4)_2$ (lanes 11-15). After the reactions, the extent of DNA demethylation of the plasmid DNA was analyzed by the restriction digestion-PCR assay outlined in FIG. 5A. The histograms show the relative proportions of the plasmid DNA resistant to HpaII cleavage. For comparison of bars 2-5 to bar 1, *, $p<0.05$; **, $p<0.01$ by the t-test. FIG. 6B: Effects of BER inhibitors on the demethylation activities of the porcine sperm nuclear extract. The DNA demethylation reactions were carried out by incubating fully-methylated plasmid DNA pMR1-8 and sperm nuclear extract containing 10 mM $CaCl_2$ and increasing concentrations of APE-i (0, 10 µM 100 µM, and 1 mM, lanes 2-6) or 3-AB (0, 5 µM, 500 µM, 5 mM, and 50 mM, lanes 8-12). After the reactions, the extents of demethylation of the plasmid DNA were analyzed by the restriction digestion-PCR assay. FIG. 6C: Effect of the CDA inhibitor THU on the demethylation reaction in the porcine sperm nuclear extract. The fully-methylated pMR1-8 DNA was subjected to incubation in the extract at 37° C. for 2 h containing, increasing concentrations of THU (0, 30 µM, 100 µM and 1 mM, lanes 1-4). The extents of demethylation of the plasmid DNA were analyzed by the restriction digestion-PCR assay. The histogram shows the relative proportions of plasmid DNA resistant to HpaII cleavage. M, mock control without incubation. Error bars indicate S.D.

DETAILED DESCRIPTION OF THE INVENTION

Figure 3A:
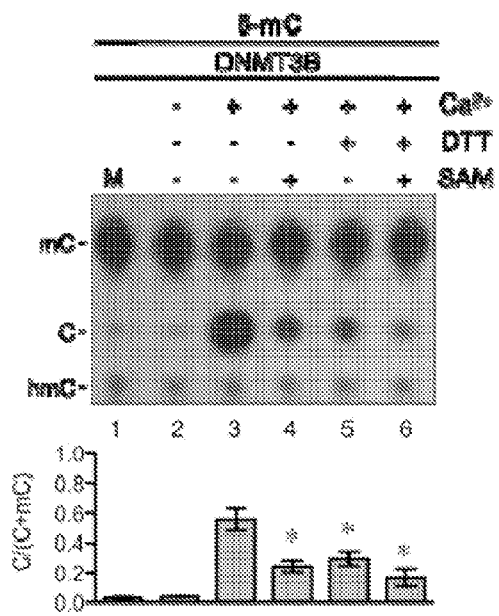
FIGS. 3A-B show the effects of a reducing condition and SAM on the DNA demethylation and methylation activities of DNMT3B.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

Definitions

The terms is used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms May be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent preferably within 10 percent, and more preferably within 5 percent of a given value or range. Numerical quantities given herein are approximate, meaning that the term "around", "about" or "approximately" can be inferred if not expressly stated.

The term "5mC" refers to 5-methylcytosin.

The term "agent" refers to any matter, substance or thing producing or used for obtaining specific results, which includes, but not limited to, compounds, co-factors, etc.

The invention relates to the discovery that mammalian DNMTs, including DNMT1, DNMT3A, and DNMT3B can actively and directly convert 5-mC on DNA into C biochemical reaction. See Chen et al, (2013) THE JOURNAL OF BIOLOGICAL CHEMISTRY VOL. 288, NO. 13, pp. 9084-9091, which is incorporated herein by reference in its entirety.

Specifically, the invention relates to the discovery that in in vitro reactions, the mouse and/or human DNMT1, DNMT3A and DNMT3B all could act as an active DNA demethylase, removing the methyl group from 5-mC on DNA in an $Ca^{2+}$ ion and redox state-dependent manner.

The invention also relates to the discovery of the DNA 5-mC demethylation activities of DNMTs that could be used to screen, identity, and design reagents, including chemical compounds and therapeutic agents, which would modulate the DNA 5-mC demethylation activities of DNMTs and their modified forms/derivatives, for the purpose of regulating the different cellular processes including gene expression, chromosome structure, carcinogenesis (metastasis), cell division, cell motility, neuronal plasticity, etc.

The protein sequences of DNMTs are as follows: DNMT1 [Homo sapiens] SEQ ID NO: 4; DNMT1 [Mus musculus] SEQ ID NO: 5; DNMT3A [Homo sapiens] SEQ ID NO: 6; DNMT3A [Mus musculus] SEQ ID NO: 7; DNMT3B [Homo sapiens] SEQ ID NO: 8; DNMT3B [Mus musculus] SEQ ID NO: 9.

To generate modified DNMTs we serially deleted 10 amino acids from N-terminal of the full-length DNMTs. For example, the modified forms of human DNMT1 is DNMT1 (11-1620), DNMT1(21-1620), DNMT1(31-1620) . . . , etc. All the deletion-modified DNMT1s are tested for DNA methylation and demethylation activities in vitro and in vivo. In addition, DNMT1 may be modified by deletion of the internal 10 amino acid of the full length DNMA1, and the modified forms are DNMT1($\Delta$11-20), DNMT1($\Delta$21-30). DNMT1($\Delta$31-40) . . . , etc. The same deletion modifications may be used to generate deletion modified forms of DNMT3A and DNMT3B.

To screen, identify, and/or design reagents that modulate the DNA 5-mC demethylation activities of DNMTs, several assays can be used, which include in vitro and in vivo assays.

(1) In Vitro

The DNMTs and 5-mC containing DNA substrates are incubated with the test agents under proper reaction conditions. The DNMTs used may be in the forms of either recombinant wild-type/modified/genetically engineered enzymes or as ectopically expressed wild type/modified/genetically engineered enzymes in cellular or nuclear extracts prepared from vertebrate cell cultures/tissues, yeast cells, or bacterial cells. The methyl group on the 5-mC-containing DNA substrates can be radioactive, or labeled by other methods.

After the reaction, the DNA substrates are isolated manually or automatically, and the content of methylation/demethylation is determined by several methods, such as restriction digestion-based analysis, antibody-based analysis. Scintillation counting, autoradiography, dot blotting, liquid chromatography-based analysis. Na bisulfite-based analysis and hydrolysis-TLC (thin layer chromatography). The effect of each test agent on the DNA 5-mC demethylation activities of the DNMT enzymes is determined by comparison of the content of 5-mC on the DNA substrate with the control (mock), before and after the in vitro reaction.

(2) In Vivo

The reporter DNAs methylated at 5-C are introduced into cells containing either the endogenous DNMTs alone or with exogenously expressed wild type/modified/genetically engineered DNMTs. The reagents to be tested are added into the cell culturing medium, or sent into the cells, before triggering the DNA demethylation activities of the DNMTs.

The methylated reporter DNAs carry genes, such as different fluorescence genes, luciferase gene, drug-resistant gene, or genes of cell survivals etc., the expression levels of which can indicate the methylation/demethylation status of the DNA substrates. Alternatively, the methylated report DNAs can be isolated manually or automatically, and analyzed with respect to their 5-mC content by methods described above.

EXAMPLES

Materials and Methods

Recombinant Plasmids and Recombinant Proteins.

Constructions of expression plasmids used in this study were described in Chen et al. (*J Biol Chem.* VOL. 287, pp. 33116-33121, 2012. It is incorporated herein by reference in its entirety), which included plasmids for exogenously expressing DNMT1, DNMT3A, and DNMT3B. The DNA methylation-inactive mutants of the DNMTs, i.e. DNMT1-PSC, DNMT3A-PS and DNMT3B-PS, were generated by insertion of a serine residue before the Cys-1229 at the catalytic site of DNMT1 or by replacing the cysteine residue Cys-706 and Cys-657 in the catalytic domains of DNMT3A and DNMT3B, respectively, with a serine residue.

Figure 7:
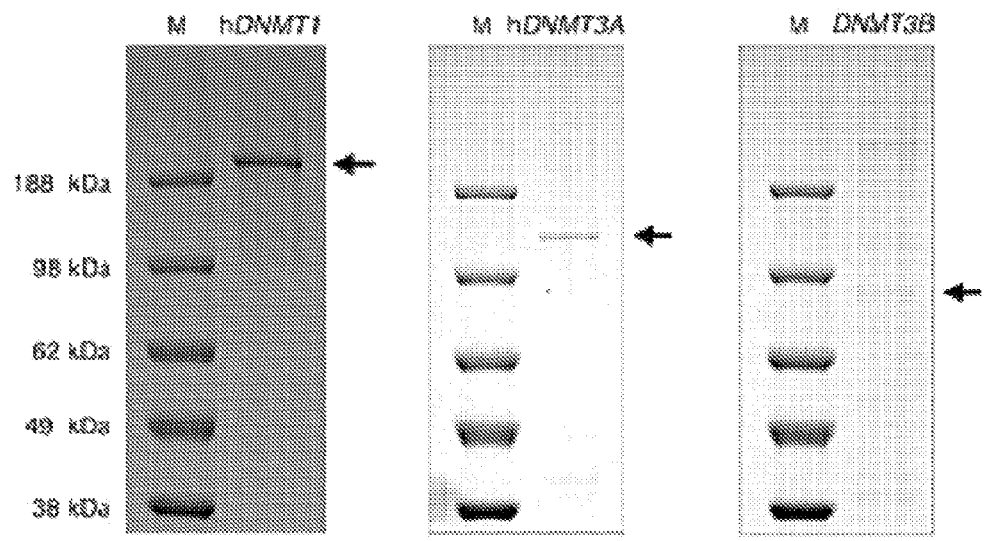
FIG. 7 shows the results of SDS-PAGE analyses. The recombinant human hDNMT1 (500 ng), human hDNMT3A (250 ng), and mouse DNMT3B (250 ng) were subjected to SDS-PAGE followed by the coomassie blue staining. The arrows indicate the expected bands of the three DNMTs, respectively. Protein markers were loaded in the M lanes.

All of the recombinant enzymes DNMTs, including hDNMT1 (purity ~78%), hDNMT3A (purity ~90%), and mouse DNMT3B (purity ~50%) (FIG. 7), were purchased from BPS Bioscience.

Cell Culture and DNA Transfection.

The human embryonic kidney 293T cells were cultured under 5% $CO_2$ at 37° C. in DMEM medium supplemented with 10% FBS and 1% Penicillin-Streptomycin. For DNA transfections, different expression plasmids were delivered into cells using either LIPOFECTAMINE® 2000 or MAXI-FECT™. The transfected cells were collected 2 days afterwards for further experimentation.

Preparation of Nuclear Extracts.

The nuclear extracts were prepared from the porcine sperms and 293T cells, respectively, by a modified method. Briefly, the porcine semen was washed three times by PBS buffer and the sperm pellet isolated with FICOLL®. The pellet was resuspended in a hypotonic buffer (10 mM Tris-HCl, pH7.4, 10 mM NaCl, 10 mM EDTA and EDTA-free protease inhibitors) on ice for 15 minutes. The resuspended sperms were passed through a G21 needle 10 times and then centrifuged at 13,200 rpm at 4° C. for 10 min. The supernatant was removed and the pellet of the nuclei was resuspended in a resuspension buffer (10 mM Tris-HCl, pH7.4, 10 mM NaCl, 1.5 mM, $MgCl_2$ and EDTA-free protease inhibitors), and an equal volume of 1M NaCl was added for 30 min incubation on ice. The solution was centrifuged at 13,200 rpm at 4° C. for 30 min and the supernatant (nuclear extract) was dialyzed at 4° C. in buffer B (10 mM Tris-HCl, pH7.4, 50 mM NaCl, 1.5 mM $MgCl_2$ and EDTA-free protease inhibitors) overnight with 2 changes of the dialysis buffer.

The preparation of nuclear extract from 293T cells followed the procedures described above. The transfected cells were washed 3 times with PBS and resuspended in the hypotonic buffer on ice for 10 mins. The solution was centrifuged at 4,000 rpm for 10 mins and the supernatant were removed. The nuclear pellet was resuspended in the resuspension buffer and then an equal volume of 1M NaCl was added for 30 min incubation on ice. The lysate was centrifuged at 13,200 rpm at 4° C. for 30 min and the supernatant was collected as a nuclear extract, which was then dialyzed at 4° C. in buffer B overnight.

DNA Substrates for In Vitro DNA Demethylation Assay.

The 5-mC-containing substrate for DNA demethylation assay of the porcine sperm nuclear extract was prepared from the 2,819 bp pMR1-8 plasmid containing 185 CpG dyads and 11 MspI restriction sites. The unmodified pMR1-8 plasmid was amplified in the SCS110 bacteria and then methylated by the bacterial methyltransferase M.SSS I in NEB buffer 2 supplemented with 160 µM SAM (S-adenosylmethionine). The extent of methylation of the plasmid was checked by HpaII digestion.

C-5 methylated double-stranded DNA substrate was used in the demethylation reactions with 293T nuclear extract or the recombinant DNMTs (see below), and then analyzed by the hydrolysis-TLC assay.

In Vitro Reactions of 5-mC to C Conversion on DNA.

For DNA demethylation reactions, 40 ng of the methylated pMR1-8 plasmid DNA or 5-mC containing double-stranded DNA substrate was incubated with 100 µg of the nuclear extracts or 40 nM recombinant DNMTs proteins in 50 µl of buffer B containing 100 µg/ml BSA at 37° C. up to 4 h. When needed, 10 µM-10 mM of three divalent cations ($Ca^{2+}$, $Mg^{2+}$, or $Fe^{2+}$), 10 µM-1 mM CRT0044876 (APE-i), 0.5 µM-50 mM 3-aminobenzamide (3-AB), 30 µM 1 mM tetrahydrouridine (THU), 5 mM DTT, or 160 µM SAM was included in the reaction mixtures. To assay the effect of redox-state of the enzymes, 40 nM recombinant DNMTs was pre-treated with 10 µM-10 mM $H_2O_2$ in 50 µl of buffer B containing 100 µg/ml BSA at 15° C. for 30 min. Forty ng of the 5-mC containing double stranded DNA substrate was then added and the reaction mixtures were incubated at 37° C. for 4 h.

All reactions were stopped by 1.3% SDS and treated with proteinase K at 50° C. for 20 min. The DNA substrates and demethylated products at the end of the reaction were isolated using the Qiaquick Nucleotide Removal Kit, and subjected to restrictions digestion-PCR assay or hydrolysis-TLC assay (see below).

C-5 Methylated Double-Stranded DNA Substrate Preparation.

The 5-mC-containing DNA substrate was prepared by PCR amplification of a 561 bp fragment from the pMR1-8 plasmid containing MspI/HpaII sites (SEQ ID NO: 1). During the PCR amplification, a 5-mC-containing dNTP mix (Zymo Research) was used. Primers for PCR were: pMR1-8 F, 5'-aaagataccaggegtttcccc-3' (SEQ ID NO: 2); and pMR1-8 R, 5'-gagttttcgttccactgagegtc-3' (SEQ ID NO: 3).

In Vitro Reactions of C to 5-mC Conversion on DNA.

Methylation in vitro of unmodified pMR1-8 plasmid DNA by the DNMTs were carried out and analyzed by the hydrolysis-TLC assay. When needed, 1 mM $CaCl_2$ or 5 mM DTT was also included in the reaction mixture.

Restriction Digestion-PCR Assay of (C-5 Methylation on Double-Strand DNA Substrate(s).

Figure 5A:
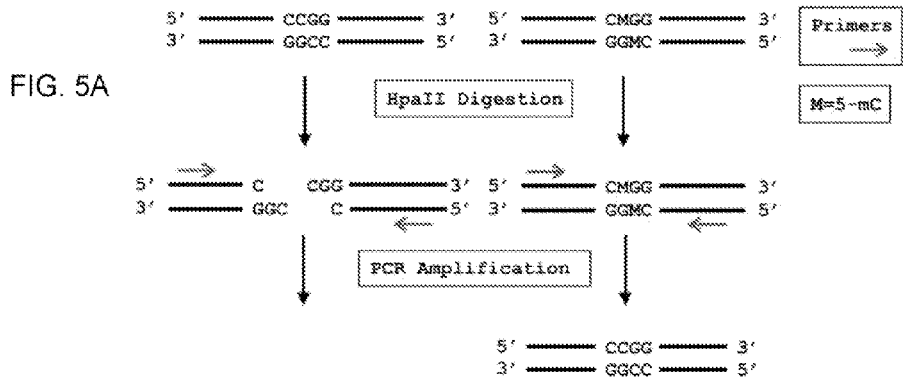
FIGS. 5A-B show experimental strategies for assay of the inter-conversions of 5-mC and C.

The procedures are as described previously (Chen et al., 2012, ibid). See FIG. 5A legend for more details.

Hydrolysis-TLC (Thin Layer Chromatography) Assay of 5-mC, 5-hmC, and C on DNA.

The procedures were similar to those described in Chen et al. (2012). ibid. See FIG. 5B legend for details.

Results

In Vitro DNA Demethylation by Porcine Sperm Extract.

Figure 6A:
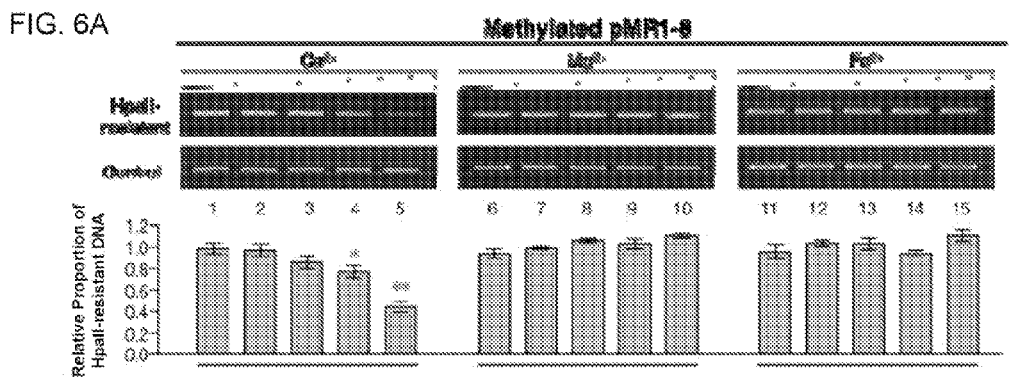
FIGS. 6A-C show the DNA demethylation activity of porcine sperm extracts.
Figure 6B:
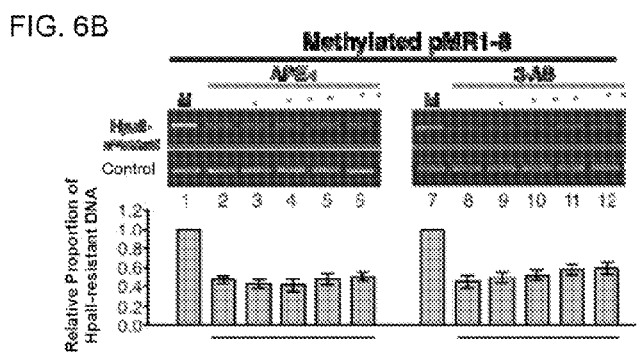

We performed in vitro DNA C-5 demethylation reactions using the nuclear extract prepared from porcine sperms. The effect of $Ca^{2+}$ ion were also tested. Remarkably, inclusion of 1-10 mM of $Ca^{2+}$, but not $Mg^{2+}$ (compare lanes 7-10 to lane 6) or $Fe^{2+}$ (compare lanes 12-15 to lane 11, FIG. 6A), significantly reduced the extent of DNA methylation by 20-50% (compare lanes 4 and 5 to lane 1, FIG. 6A). Furthermore, inclusion of inhibitors of either the BER pathway, CRT0044876 (APE-i) and 3-aminobenzamide (3-AB), or the cytidine-deaminase (CDA), tetrahydrouridine (THU), in the reactions had little effect on the in vitro DNA demethylation activity of the sperm nuclear extract (FIGS. 6A and 6B). The data of FIGS. 6A-B suggested that $Ca^{2+}$ ion stimulated a BER-independent and CDA-independent DNA demethylation activity in the nuclear extract of the porcine sperms.

It was not trivial to purify the factor(s)/enzyme(s) in the nuclear extract of the porcine sperms that was responsible for the in vitro conversion of 5-mC to C on DNA. Since the porcine sperm nuclear extract contained DNMT1/DNMT3A/DNMT3B (data not shown) and the murine/human orthologs of the latter two DNMTs acted in vitro as DNA 5-hydroxymethylcytosine (5-hmC) dehydroxymethylases under oxidative conditions in the absence of SAM, we suspected that under appropriate conditions, these DNMTs might also be capable to convert other modified forms of cytosine, e.g., 5-mC, to C.

Figure 5B:
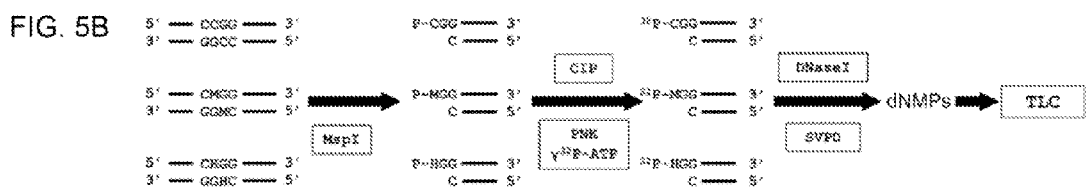
Figure 6C:
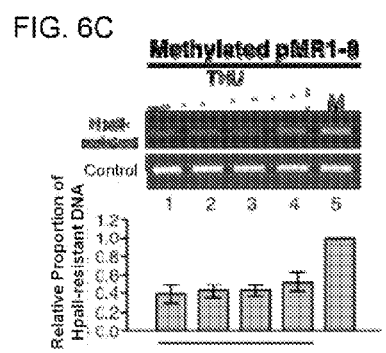

In view of the data of FIG. 6, we performed in vitro DNA demethylation reactions in the presence of 10 mM of $Ca^{2+}$. 5-mC-containing double-stranded DNA substrate was incubated with nuclear extracts prepared from 293T cells transfected with plasmids overexpressing EGFP (a negative control), mouse DNMT1, mouse DNMT3A, mouse DNMT3B, as well as their mutants, respectively. After the reactions, the DNA products were hydrolyzed as depicted in FIG. 5B and the nucleotides were analyzed by TLC (FIG. 1). As shown, under the reaction conditions tested, the nuclear extracts containing the exogenously expressed DNMT1 (lane 4, FIG. 1), DNMT3A (lane 6, FIG. 1), and DNMT3B (lanes 8, FIG. 1) all could remove the 5-methyl group from approximately 30% of the 5-mC residues on the DNA substrates.

Remarkably, the DNA demethylase activities of the 3 mouse DNMTs were greatly diminished, by approximately 73% to 88%, when amino acid substitutions or insertion were introduced into the known catalytic sites of C-5 methylation of these enzymes (compare lanes 10, 12, 14 to 4, 6, 8, respectively, FIG. 1). The data of FIG. 1 suggested that the two de novo DNMTs as well as the maintenance DNMT1 could act as active DNA 5-mC demethylases under appropriate conditions. The de novo DNMTs, DNMT3A and DNMT3B can transfer the methyl-group to DNA which do not contain any DNA methylation on both strands. After de novo methylation, the DNA is methylated on both DNA strands. The maintenance DNMT1 can methylate the hemimethylated (one of double strands is methylated) DNA during the DNA replications.

$Ca^{2+}$- and Redox State-Dependent DNA 5-mC Demethylase Activities of Partially Purified Recombinant DNMTs.

To further confirm the result of FIG. 1, recombinant mouse DNMT3B, human DNMT1 (hDNMT1), and human DNMT3A (hDNMT3A) partially purified from recombinant baculovirus-infected Sf9 insect cells were examined for their DNA demethylation activities. First, the recombinant mouse DNMT3B (~50% purity, FIG. 7) was subjected to incubation with 5-mC-containing DNA substrate in buffer B containing increasing concentrations (0, 10 μM, 100 μM, 1 mM, 5 mM and 10 mM) of $CaCl_2$ (FIG. 2A). As seen, the recombinant DNMT3B exhibited significant DNA demethylation activity only in the presence of $Ca^{2+}$ (compare lanes 3-7 to lane 2, FIG. 2A), with the activity highest in the presence of 1 mM $Ca^{2+}$ (lane 5, FIG. 2A). We tested and compared the DNA demethylation activities of DNMT3B, hDNMT1 (~70% purity, FIG. 7) and hDNMT3A (~90% purity, FIG. 7) in buffer B containing 1 mM $CaCl_2$ (FIG. 2B). Both hDNMT1 and DNMT3B exhibited high DNA demethylation activity, converting at least 50% of 5-mC on DNA to C (lanes 2 and 4, FIG. 2B), while the recombinant hDNMT3A showed relatively lower activity (approximately 20% conversion, lane 3 of FIG. 2B). Demethylation reaction by the recombinant mouse DNMT3B also removed the HpaII resistance of the methylated DNA substrate (data not shown). These data together demonstrated that mammalian DNMTs could function as active DNA demethylases in vitro.

Figure 3B:
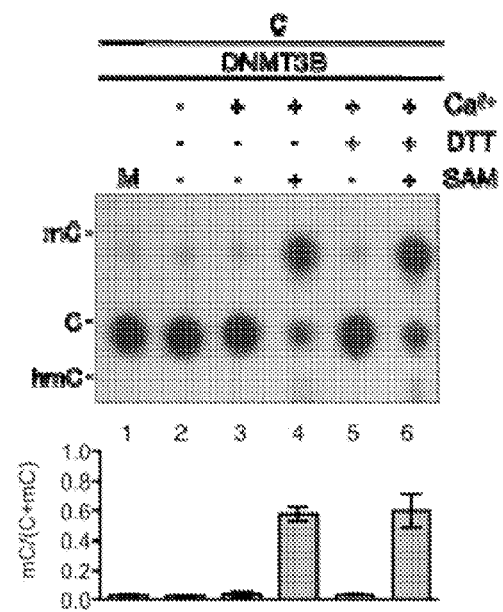

The DNA demethylation activities of the DNMTs appeared to be affected by the redox state of the enzymes. As exemplified by DNMT3B, pre-incubation of the enzyme with the reducing dithiothreitol (DTT) greatly decreased the extent of conversion of 5-mC to C (compare lane 5 to lane 3. FIG. 3A), although addition of $H_2O_2$ as high as 10 mM to the reaction mixture did not affect the DNA demethylation activity of the enzyme (data not shown). In contrast to 5-mC demethylation, the 5-C methylation reaction of DNMTs did not require $Ca^{2+}$, nor was it affected by DTT (compare lane 6 to lane 4, FIG. 3B).

Reversibitiy of the DNA 5-mC Demethylation and 5-C Methylation Reactions Catalyzed by DNMTs.

Figure 8:
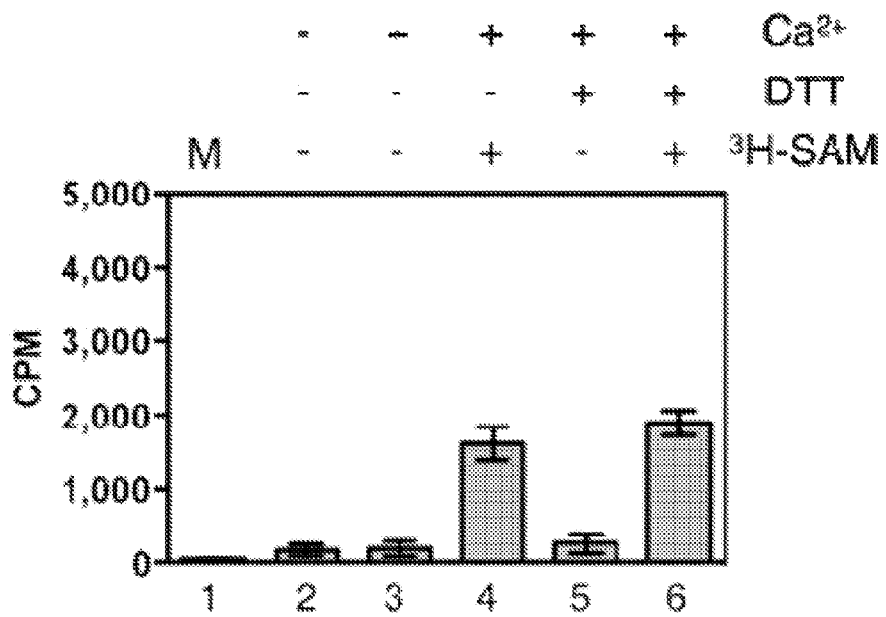
FIG. 8 shows DNA demethylation by recombinant DNMT3B in the presence of $^3$H-SAM. The reaction conditions were the same as those described in FIG. 3A, except that 1 µCi $^3$H-SAM was also included in each of the reaction mixtures. After the reactions, the mixtures were further incubated with 100 µl of 0.5N NaOH at 55° C. for 10 mins and neutralized with 100 µl of 1M Tris-Cl pH7.0. The DNA substrates were then precipitated with 10% trichloroacetic acid (TCA) in 5 mM Na pyrophosphate on ice for 15 mins, and loaded onto DE-81 ion-exchange papers followed by air drying. The DE-81 papers were washed 5 times with 5% TCA in 5 mM Na pyrophosphate, twice with 100% EtOH, air dried, and the $^3$H counts on DNA were determined in a liquid scintillation counter.

As exemplified for DNMT3B in FIG. 3A, the inclusion of SAM, the methyl donors needed for DNA 5-C methylation by the DNMTs, in the reaction mixture greatly reduced the extent of conversion of 5-mC to C (compare lanes 4 and 6 to lane 3 FIG. 3A). This could be due to the inhibition of the demethylation activity of the DNMTs by SAM. Alternatively, the presence of SAM in the demethylation reaction might favor the methylation function of DNMTs, thus pushing the demethylation backwards. The latter scenario was confirmed with inclusion of radioactive $^3$H-SAM in the reaction mixtures and quantitation of $^3$H-labeled-$CH_3$ on DNA after the reactions (lanes 4 and 6, FIG. 8). This result suggested that the DNA 5-mC demethylation reaction was reversible, with the presence SAM pushing the DNMT3B to re-methylate the demethylated cytosine on the DNA substrate.

Figure 4A:
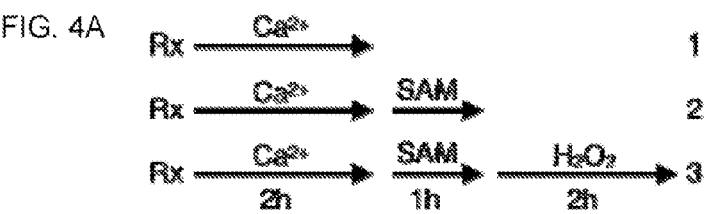
FIGS. 4A-B show reversibility of the DNA demethylation and methylation reactions in vitro.
Figure 4B:
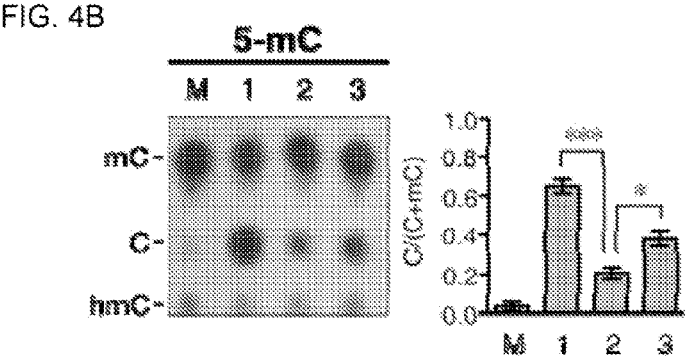

The reversibility of the DNA methylation-demethylation reactions as catalyzed by the mammalian DNMTs was further studied by an analysis of the dynamic changes of the DNA methylation in vitro. In FIG. 4A, the double-stranded DNA substrate containing 5-mC was first incubated with the recombinant DNMT3B in a demethylation buffer for 2 h. SAM was then added and the incubation continued for 1 h. Finally, $H_2O_2$, which was known to inhibit the methylation reaction, was added and the reaction continued for another 2 h. As exemplified in the TLC plate and statistically presented in the histogram of FIG. 4B, approximately 60% of 5-mC on the DNA substrate were demethylated by DNMT3B at the end of the first reaction (compare lane 1/bar 1 to lane M/bar M, FIG. 4B). The continued 1 h incubation in the presence of SAM converted more than 60% of the C back to 5-mC (compare lane 2/bar 2 to lane 1/bar 1, FIG. 4B). Finally, the addition of $H_2O_2$ led to the switch of the enzyme activity of DNMT3B from methylation to demethylation again (compare lane 3/bar 3 to lane 2/bar 2, FIG. 4B), presumably due to loss the DNA methylation function of the oxidized enzyme. The data of FIGS. 3 and 4 altogether suggested that the switch of the catalytic functions of the DNMTs in between DNA methylation and demethylation was flexible, subjecting to the regulation by a range of factors including the local concentration of $Ca^{2+}$, the presence of SAM, and the redox-state of the DNMTs.

Generation of Radioactive-Labeled Methylated DNA Substrate.

Two different methods were used to generate radioactive-labeled methylated DNA as follows: The unmethylated DNA is incubated with M.SSSI and radioactive SAM, such as $^3$H-SAM or $^{14}$C-SAM. After the incubation and DNA isolation, the radioactive signal of the DNA was determined by autoradiography or scintillation counting to quantitate methylated DNA. Optionally, the extent of the methylation of the DNA may be observed by HpaII digestion followed by gel electrophoresis. Alternatively, to make radioactive methylated DNA, PCR amplification is performed by using dNTP mix containing 5-[$^3$H]-methyl-dCTP or 5-[$^{14}$C]-methyl-dCTP. After purification of the PCR product, the extent of methylation of the DNA is analyzed by radioactive signal autoradiography or scintillation counting, and optionally observed the methylation level by HpaII digestion followed by gel electrophoresis.

Methylated Reporter Gene DNA Substrate.

A plasmid containing a reporter gene expressing a reporter protein such as EGFP or GFP (e.g., commercial available pEGFP-C1) was highly methylated by the enzyme M.SSSI in the presence of SAM using a method described above. Then the highly methylated and unmethylated reporter plasmids were transfected into 293 cell by Lipofectamine 2000, respectively. To detect expression of the reporter gene, the transfected cells were analyzed by a fluorescence microscopy and FACS flow cytometry. The results showed that the unmethylated EGFP reporter gene could strongly express the EGFP protein in the cells, but the highly methylated EGFP reporter gene expression of the EGFP protein was severely suppressed.

Based on the correlation between the DNA methylation level of the reporter gene and gene expression, we co-transfect the highly methylated reporter plasmid EGFP and the DNMTs-expression plasmids to 293 cells by Lipofectamine 2000. After 24 h, the transfected cells are treated with different test agents (chemical compounds) or different genetically modified viruses transduced with exogenous cDNA encoding a known protein of interest.

The cells co-transfected with methylated EGFP plasmids and DNMT3B-expression plasmid without any chemical or virus treatment showed 2-3 folds of EGFP-positive cell population comparing to the cells co-transfected with methylated EGFP plasmids and control plasmids (without DNMTs) without any chemical or virus treatment.

If the compound (test agent) or genetically modified virus could affect the DNA demethylation, the population of EGFP-positive cells will be changed. By comparing the EGFP-positive cell populations in the presence and absence of chemical (or virus) treatment, it is feasible to identify a compound (a test agent) which may enhance DNA demethylation (i.e., increasing GFP-positive cell population) or reduce the DNA demethylation (decreasing GFP-positive cell population).

In addition, the expression of reporter (EGFP) can be analyzed by western blotting.

The DNA methylation level of the reporter plasmids could also be determined by an in vitro method. After chemical or virus treatments, the methylated plasmids are isolated from the 293 cells. The DNA methylation level of isolated reporter plasmids can be determined by the several methods described above, such as a restriction digestion-polymer chain reaction (PCR) assay, a hydrolysis-thin layer chromatography assay, antibody-based analysis, scintillation counting, autoradiography, dot blotting, liquid chromatography-based analysis, Na bisulfite-based analysis.

Other candidate genes for reporters may be used, for example: (1) Neomycin-resistance gene, which can keep the cell survive under Neomycin (G418) treatment; (2) Puromycin resistance gene. The cell with expression of this gene can survive under Puromycin treatment: (3) Blasticidin resistance gene, which can make cell survive under Blastindin selection; (4) Luciferase gene-pGL3 reporter vector (Promega). The firefly (*Photinus pyralis*) luciferase can catalyze the two-step oxidation reaction to yield light (550-570 nm); (5) Red Fluorescence gene-pDsRed-C1. The protein is red fluorescence protein (excitation-557 nm, emission-592 nm); and (6) Green fluorescent protein (GFP)-encoding gene.

Antibody-Based Analysis.

DNAs with different methylation levels are immunoprecipitated by the 5-mC antibody. The precipitated DNA may be analyzed by PCR or pyro-sequencing to determine the relative methylation level.

Dot Blotting.

DNAs with different methylation levels are loaded onto NC membranes in serial diluted amounts and cross-linked by UV. The membranes are hybridized with 5-mC antibody and exposed with X-Ray films. The strong dot signal indicates a strong methylation level on the DNA.

Scintillation Counting, Autoradiography.

A Scintillation counter is a common-used instrument that can measure ionizing radiation. A radioactive-labelled DNA, such as $^3$H or $^{14}$C methylated DNA, is load into a container containing a scintillation cocktail. The radioactive signal is determined with a Scintillation counter by detection of light emission. In addition, radioactive-labelled DNA may be load into a gel or on a NC membrane, and exposed with an X-Ray film.

Liquid Chromatography-Based Analysis.

The affinity of each deoxynuclesides (dC, dmC, dT, dG, and dA) to bind a C18 column is different. In this assay, DNA is degraded by DNaseI and Nuclease P1 to generate deoxynucleasides. The degraded mixture is subjected to an HPLC system with a C-18 column. After injection of the mixture, deoxynucleasides are eluted individually at different time points by a hydrophilic buffer.

Na Bisulfite-Based Analysis.

DNAs with different methylation levels are treated with Na-bisulfite. The unmethylated cytosine is deaminated to uracil, but not the methylated DNA. The bisulfite treated DNAs are further amplified by PCR and sequenced by cloning. In the final sequence result, the original un-methylated cytosine will present "T", and the original methylated cytosine will present "C". Based on this bisulfite-generated polymorphisms, the DNA methylation level can be analyzed by sequencing, PCR amplification with site-specific primers, HRM (high resolution melt), restriction digestion (COBRA), non-denaturing gel (MS-SSCA), or MALDI-TOF.

The current study has revealed a totally unexpected characteristic of mammalian DNMTs, likely those of the vertebrates in general. That is, the vertebrate DNMTs, in addition to converting C to 5-mC on DNA, can also actively demethylate 5-mC on DNA under specific conditions (FIGS. 1 and 2), in particular in the presence of $Ca^{2+}$ ion and under non-reducing condition (FIG. 3). In other words, the covalent addition of the methyl group to the C-5 position of cytosine on DNA, as catalyzed by DNMTs, is reversible (FIG. 4). The loss of the DNA demethylation activities of the mutant forms in comparison to the wild type enzymes (FIG. 1) also suggests that each of the 3 DNMTs utilizes the same domain or overlapping domains to catalytically methylate and demethylate DNA.

Based on our data presented above, in particular the $Ca^{2+}$ dependence of the DNA demethylation activities of the 3 DNMTs and in the porcine sperm nuclear extract, we suggest that in addition to other pathways, e.g. the conversion of 5-mC to 5-hmC by TET and 5-hmC to C by DNMT3A and DNMT3B, direct conversion of 5-mC to C by the active DNA demethylation activities of the 3 DNMTs also play a major role in the genome-wide demethylation during early embryonic development of the vertebrates.

In summary, we have discovered that the mammalian DNMT1, DNMT3A, and DNMT3B, contrary to the conventional thought of their being mainly DNA methyltransferases, also act in vitro as active DNA demethylases in a $Ca^{2+}$ ion- and redox state-dependent manner.

What is claimed is:

1. A method for identifying a test agent as a modulator of the active DNA demethylation activity of a DNA methyltransferase, comprising:
   (a) providing a methylated DNA;
   (b) providing the DNA methyltransferase;
   (c) allowing the methylated DNA to react with the DNA methyltransferase in the presence of calcium ions for a sufficient time to perform a demethylation reaction and generate a demethylated DNA product in the presence or absence of a test agent;
   (d) analyzing the extent of demethylation; and
   (e) comparing the extents of the demethylation in the presence and absence of the test agent, and thereby identify the test agent as a modulator of the DNA demethylation activity of the DNA methyltransferase;
   wherein the test agent is identified as an inhibitor of the active DNA demethylation activity of the DNA methyltransferase when the extent of the demethylation is less in the presence of the test agent; or the test agent is identified as a stimulator of the active DNA demethylation activity of the DNA methyltransferase when the extent of demethylation is more in the presence of the test agent.

2. The method of claim 1, wherein the analyzing step is performed by a technique selected from the group consisting of polymerase chain reaction (PCR) assay, a hydrolysis-thin layer chromatography assay, an antibody-based analysis, scintillation counting, autoradiography, dot blotting, a liquid chromatography-based analysis, and a Na bisulfite-based analysis.

3. The method of claim 1, wherein the demethylation reaction occurs in the presence of a calcium ion concentration of around 10 μM to 10 mM.

4. The method of claim 1, wherein the DNA methyltransferase is an isolated vertebrate DNA methyltransferase or a recombinant DNA methyltransferase, or is present in a nuclear extract or present in a cellular extract.

5. The method of claim 4, wherein the vertebrate DNA methyltransferase, the nuclear extract, or the cellular extract is prepared from cells selected from the group consisting of vertebrate cell cultures, vertebrate tissues, insect cells, worm cells, insect tissues, worm tissues, plant cells, plant tissues, yeast cells, and bacterial cells.

6. The method of claim 4, wherein the nuclear extract is a sperm extract.

7. The method of claim 1, wherein the methylated DNA comprises a labeled methyl group.

8. The method of claim 7, wherein the methyl group in the methylated DNA is radioactive-labeled.

9. The method of claim 1, wherein:
   (1) the methylated DNA provided in step (a) is a methylated reporter gene operably linked to a constitutive promoter and is present in a cell;
   (2) the DNA methyltransferase provided in step (b) is operably linked to a constitutive promoter and is also present in the cell;

(3) the demethylated DNA product generated in step (c) is a demethylated reporter gene, which expresses a reporter protein in the cell; and
(4) the analyzing step is performed by a technique selected from the group consisting of:
   (i) analyzing the signal of the reporter protein encoded by the demethylated reporter gene in the cell;
   (ii) analyzing the reporter protein expression by Western blot; and
   (iii) isolating the methylated and demethylated reporter gene and analyzing the extent of demethylation by polymerase chain reaction (PCR) assay, a hydrolysis-thin layer chromatography assay, an antibody-based analysis, scintillation counting, autoradiography, dot blotting, a liquid chromatography-based analysis, or a Na bisulfite-based analysis.

10. The method of claim 9, wherein the methylated reporter gene and the DNA methyltransferase are present in the cell via transfection.

11. The method of claim 1, wherein:
(1) the methylated DNA provided, in step (a) is a methylated reporter gene operably linked to a constitutive promoter and is present in a cell having an endogenous DNA methyltransferase;
(2) the DNA methyltransferase provided in step (b) is endogenously present in the cell as the endogenous DNA methyltransferase;
(3) the demethylated DNA product generated in step (c) is a demethylated reporter gene, which expresses a reporter protein in the cell; and
(4) the analyzing step is performed by a technique selected from the group consisting of:
   (i) analyzing the signal of the reporter protein encoded by the demethylated reporter gene in the cell;
   (ii) analyzing the reporter protein expression by Western blot; and
   (iii) isolating the methylated and demethylated reporter gene and analyzing the extent of demethylation by polymerase chain reaction (PCR) assay, a hydrolysis-thin layer chromatography assay, an antibody-based analysis, scintillation counting, autoradiography, dot blotting, a liquid chromatography-based analysis, or a Na bisulfite-based analysis.

12. The method of claim 9, wherein the test agent is introduced into the cell or added to a culture medium bathing the cell.

13. The method of claim 9, wherein the methylated reporter gene comprises a DNA sequence of a gene selected from the group consisting of a fluorescent protein-encoding gene, a luciferase gene, a drug-resistant gene, and genes of cell survivals.

14. The method of claim 1, wherein the methylated DNA comprises 5-methylcytosine (5mC-containing DNA.

15. The method of claim 1, wherein the DNA methyltransferase is a modified form of a wild-type DNA methyltransferase, said modified form retaining the active DNA demethylation activity of the wild-type DNA methyltransferase.

16. The method of claim 1, wherein the DNA methyltransferase is selected from the group consisting of DNA methyltransferase 1, DNA methyltransferase 3A, DNA methyltransferase 3B, and any combination thereof.

17. The method of claim 9, wherein the constitutive promoter is a cytomegalovirus promoter.

18. A method for identifying a test agent as a modulator of the active DNA demethylation activity of a DNA methyltransferase, comprising:
(I)
a) admixing a first composition comprising a methylated DNA with a second composition comprising the DNA methyltransferase in the presence or absence of a test agent;
b) allowing a demethylation reaction to occur by reacting the methylated DNA with the DNA methyltransferase in the presence of calcium ions for a sufficient time to generate a demethylated DNA product;
c) analyzing the extent of demethylation; and
d) comparing the extents of the demethylation in the presence and absence of the test agent, and thereby identify the test agent for modulating active DNA demethylation activity of the DNA methyltransferase;
wherein the test agent is identified as an inhibitor of the active DNA demethylation activity of the DNA methyltransferase when the extent of the demethylation is less in the presence of the test agent; or the test agent is identified as a stimulator of the active DNA demethylation activity of the DNA methyltransferase when the extent of demethylation is more in the presence of the test agent;

or (II)
1) providing a cell culture medium containing cells transfected with a reporter gene that is methylated and operably linked to a constitutive promoter, said cells containing an endogenous DNA methyltransferase or exogenously expressing a wild-type, a modified or a genetically engineered DNA methyltransferase;
2) exposing the cells to a test agent;
3) allowing a demethylation reaction to occur to generate a demethylated reporter gene, which expresses a reporter protein in the cells; and
4) analyzing the extent of demethylation of the reporter gene by examining the signal intensity of the reporter protein expressed by the demethylated reporter gene in the cells;
5) comparing the extents of the demethylation of the reporter gene in the presence and absence of the test agent, and thereby identify the test agent as a modulator of the DNA demethylation activity of the DNA methyltransferase;
wherein the test agent is identified as an inhibitor of the active DNA demethylation activity of the DNA methyltransferase when the extent of the demethylation is less in the presence of the test agent; or the test agent is identified as a stimulator of the active DNA demethylation activity of the DNA methyltransferase when the extent of demethylation is more in the presence of the test agent.

19. The method of claim 18, wherein the wild-type DNA methyltransferase is selected from the group consisting of DNA methyltransferase 1, DNA methyltransferase 3A, and DNA methyltransferase 3B.

20. The method of claim 1, wherein step (c) is performed under a condition that is free of a reducing agent or under a non-reducing condition.

* * * * *